US012578108B2

(12) United States Patent
Mou et al.

(10) Patent No.: US 12,578,108 B2
(45) Date of Patent: ***Mar. 17, 2026

(54) FRESH AIR VENTILATION DEVICE FOR AIR POLLUTION PREVENTION

(71) Applicant: MICROJET TECHNOLOGY CO., LTD., Hsinchu City (TW)

(72) Inventors: Hao-Jan Mou, Hsinchu City (TW); Yung-Lung Han, Hsinchu City (TW); Chi-Feng Huang, Hsinchu City (TW)

(73) Assignee: MICROJET TECHNOLOGY CO., LTD., Hsinchu City (TW)

( * ) Notice: Subject to any disclaimer, the term of this patent is extended or adjusted under 35 U.S.C. 154(b) by 695 days.

This patent is subject to a terminal disclaimer.

(21) Appl. No.: 17/888,648

(22) Filed: Aug. 16, 2022

(65) Prior Publication Data

US 2023/0304684 A1 Sep. 28, 2023

(30) Foreign Application Priority Data

Mar. 22, 2022 (TW) .................................. 111110680

(51) Int. Cl.
*F24F 11/00* (2018.01)
*A61L 9/014* (2006.01)
(Continued)

(52) U.S. Cl.
CPC .......... *F24F 11/0001* (2013.01); *A61L 9/014* (2013.01); *A61L 9/205* (2013.01); *B01D 46/0028* (2013.01); *B01D 46/0039* (2013.01); *B01D 46/429* (2013.01); *B01D 46/442*

(2013.01); *B01D 46/448* (2013.01); *B01D 46/46* (2013.01); *B01D 53/32* (2013.01); *B01D 53/8609* (2013.01); *B01D 53/8631* (2013.01); *B01D 53/864* (2013.01); *B01D 53/8671* (2013.01); *B01D 53/8675* (2013.01);
(Continued)

(58) Field of Classification Search
None
See application file for complete search history.

(56) References Cited

U.S. PATENT DOCUMENTS

2013/0055692 A1* 3/2013 Cecchi ................... B01D 46/44
55/342
2015/0300677 A1* 10/2015 Wang ........................ E06B 7/02
55/385.2
(Continued)

FOREIGN PATENT DOCUMENTS

CN 1912482 A 2/2007
CN 104633795 A 5/2015
(Continued)

*Primary Examiner* — Jelitza M Perez
(74) *Attorney, Agent, or Firm* — Birch, Stewart, Kolasch & Birch, LLP

(57) ABSTRACT
A fresh air ventilation device for air pollution prevention includes a main body, a blower, a filtering and cleaning assembly, and a gas detection module. The blower is disposed in the main body to guide air convection and form a flow-guiding path. The filtering and cleaning assembly is disposed in the flow-guiding path to filter and clean an air pollution source in the air convection guided by the blower. The gas detection module is disposed in the flow-guiding path of the main body to detect the air pollution source and transmit a gas detection data.

19 Claims, 20 Drawing Sheets

(51) Int. Cl.

| | |
|---|---|
| *A61L 9/20* | (2006.01) |
| *B01D 46/00* | (2022.01) |
| *B01D 46/42* | (2006.01) |
| *B01D 46/44* | (2006.01) |
| *B01D 46/46* | (2006.01) |
| *B01D 53/32* | (2006.01) |
| *B01D 53/86* | (2006.01) |
| *B01D 53/88* | (2006.01) |
| *F24F 3/16* | (2021.01) |
| *F24F 11/58* | (2018.01) |
| *G01N 1/22* | (2006.01) |
| *G01N 1/24* | (2006.01) |
| *F24F 110/64* | (2018.01) |
| *F24F 110/65* | (2018.01) |
| *F24F 110/66* | (2018.01) |
| *F24F 110/70* | (2018.01) |
| *F24F 110/72* | (2018.01) |
| *F24F 110/74* | (2018.01) |
| *G01N 15/075* | (2024.01) |

(52) U.S. Cl.

CPC ....... *B01D 53/8696* (2013.01); *B01D 53/885* (2013.01); *F24F 3/16* (2013.01); *F24F 11/58* (2018.01); *G01N 1/2273* (2013.01); *G01N 1/24* (2013.01); *A61L 2209/111* (2013.01); *A61L 2209/12* (2013.01); *A61L 2209/14* (2013.01); *A61L 2209/22* (2013.01); *B01D 2257/106* (2013.01); *B01D 2257/302* (2013.01); *B01D 2257/404* (2013.01); *B01D 2257/502* (2013.01); *B01D 2257/504* (2013.01); *B01D 2257/60* (2013.01); *B01D 2257/708* (2013.01); *B01D 2257/91* (2013.01); *B01D 2259/818* (2013.01); *B01D 2273/30* (2013.01); *B01D 2279/50* (2013.01); *F24F 2011/0002* (2013.01); *F24F 2110/64* (2018.01); *F24F 2110/65* (2018.01); *F24F 2110/66* (2018.01); *F24F 2110/70* (2018.01); *F24F 2110/72* (2018.01); *F24F 2110/74* (2018.01); *G01N 2001/2276* (2013.01); *G01N 15/075* (2024.01)

(56) References Cited

U.S. PATENT DOCUMENTS

| | | | | |
|---|---|---|---|---|
| 2016/0348931 A1* | 12/2016 | Lim | .......................... | F24F 11/62 |
| 2019/0240371 A1* | 8/2019 | Benedek | ........... | B01D 53/8675 |
| 2021/0063036 A1* | 3/2021 | Oh | ....................... | G06V 10/764 |
| 2021/0188050 A1* | 6/2021 | Mou | ................. | B01D 39/2055 |
| 2021/0341168 A1* | 11/2021 | Okeya | ....................... | F24F 7/08 |
| 2022/0196268 A1* | 6/2022 | Goel | ......................... | F24F 8/22 |

FOREIGN PATENT DOCUMENTS

| | | |
|---|---|---|
| CN | 208205267 U | 12/2018 |
| CN | 210569012 U | 5/2020 |
| CN | 113952793 A | 1/2022 |
| CN | 114061111 A | 2/2022 |
| KR | 20200031433 A | 3/2020 |
| TW | I708934 B | 11/2020 |

* cited by examiner

42

FRESH AIR VENTILATION DEVICE FOR AIR POLLUTION PREVENTION

CROSS-REFERENCE TO RELATED APPLICATION

This non-provisional application claims priority under 35 U.S.C. § 119(a) to Patent Application No. 111110680 filed in Taiwan, R.O.C. on Mar. 22, 2022, the entire contents of which are hereby incorporated by reference.

BACKGROUND

Technical Field

The present disclosure relates to a fresh air ventilation device capable of filtering and detecting air pollution, in particular, to a fresh air ventilation device for air pollution prevention.

Related Art

In light of people paying more and more attention to the ambient air quality in daily life, it is noted that, gases containing particulate matters (PM1, PM2.5, PM10), carbon dioxide, total volatile organic compounds (TVOC), formaldehyde, etc. or even the particulates, the aerogels, the bacteria, the viruses in the gas might result in adverse effects on the human health, even might be life-threatening when exposure to these gases.

As stated above, currently, it is not easy to control the indoor air quality since the factors affecting the indoor air quality include not only the outdoor space air quality but also the air conditioning and the pollution source in the indoor space (especially the dust, bacteria, and viruses originated from poor circulation of air in the indoor space).

Consequently, it is an issue of the present invention to provide a solution that can instantly purify and improve the air quality of the indoor space, reduce the risks of inhaling hazardous gases, and monitor the air quality of the indoor space anytime and anywhere.

SUMMARY

One object of the present disclosure is to provide a fresh air ventilation device for air pollution prevention, wherein a gas detection module is provided to detect the air quality of the indoor space and verify the condition of the ambient air quality. At least one blower is utilized to guide the air pollution source, so that the air pollution source can be filtered through a filtering and cleaning assembly in real-time. A micro-controller is further provided to receive the data detected by at least one gas detection module to enable the at least one blower and adjust the air volume of the at least one blower. Therefore, the ambient air quality can be detected in real-time and the air pollution source can be filtered in real-time.

In order to accomplish the above object, in one general embodiment of the present disclosure, a fresh air ventilation device for air pollution prevention is provided. The fresh air ventilation device includes a main body, at least one blower, a filtering and cleaning assembly, and at least one gas detection module. The at least one blower is disposed in the main body to guide the air convection so as to form a flow-guiding path. The filtering and cleaning assembly is disposed in the flow-guiding path to filter and clean an air pollution source in the air convection guided by the at least one blower. The at least one gas detection module is disposed in the flow-guiding path of the main body to detect the air pollution source and transmit a gas detection data.

In order to accomplish the above object, in another general embodiment of the present disclosure, a fresh air ventilation device for air pollution prevention is provided. The fresh air ventilation device includes a main body, at least one blower, a filtering and cleaning assembly, at least one gas detection module, and a micro-controller. The at least one blower is disposed in the main body to guide the air convection so as to form a flow-guiding path. The filtering and cleaning assembly is disposed in the flow-guiding path to filter and clean an air pollution source in the air convection guided by the at least one blower. The at least one gas detection module is disposed in the flow-guiding path of the main body to detect the air pollution source and transmit a gas detection data. The micro-controller wirelessly receives the gas detection data from the at least one gas detection module and performs an intelligent comparison under a surveillance condition so as to transmit a driving command to enable the at least one blower and adjust an air volume of the at least one blower.

BRIEF DESCRIPTION OF THE DRAWINGS

The disclosure will become more fully understood from the detailed description given herein below, for illustration only and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1A:
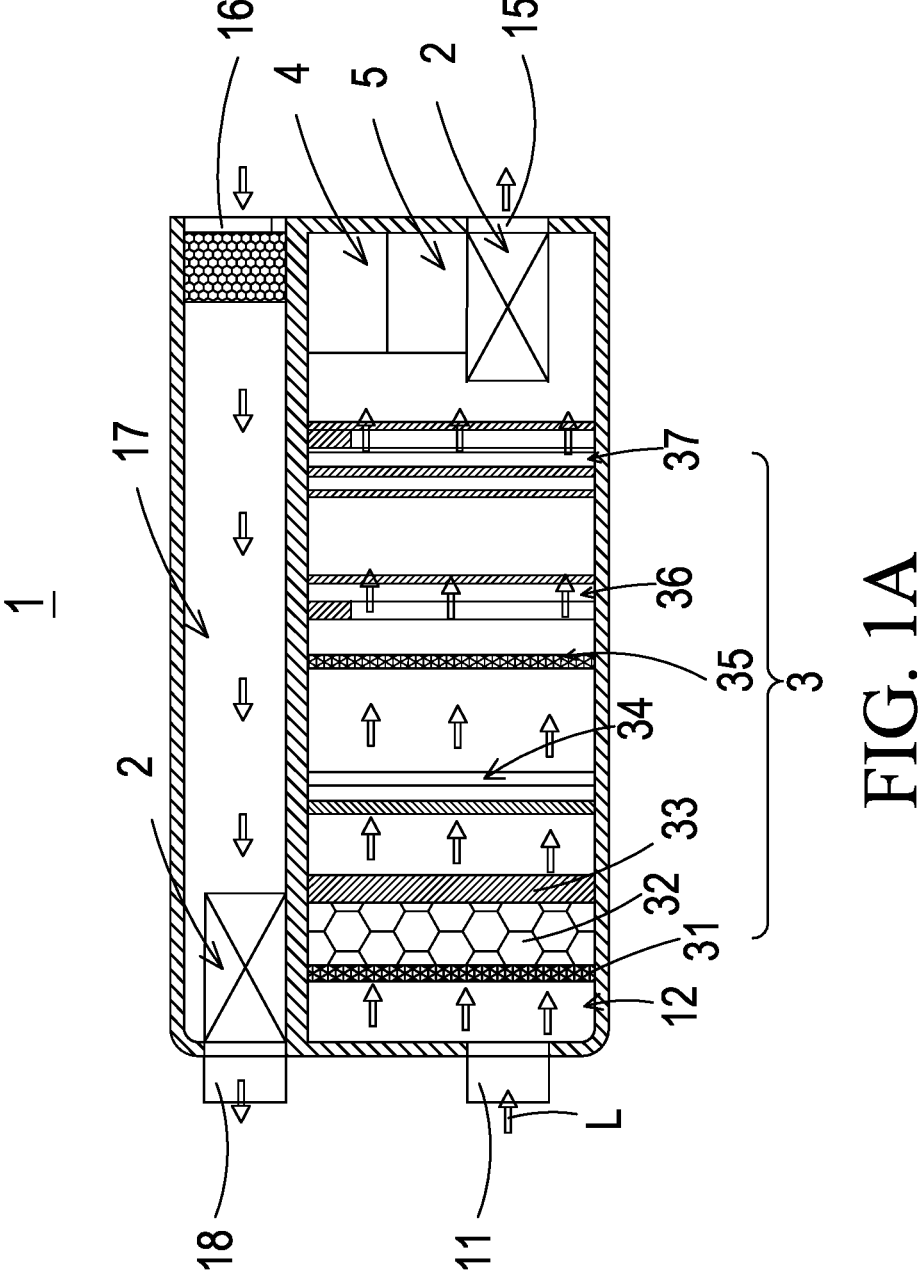
FIG. 1A illustrates a schematic view of a fresh air ventilation device for air pollution prevention of an exemplary embodiment in the present disclosure.
Figure 1B:
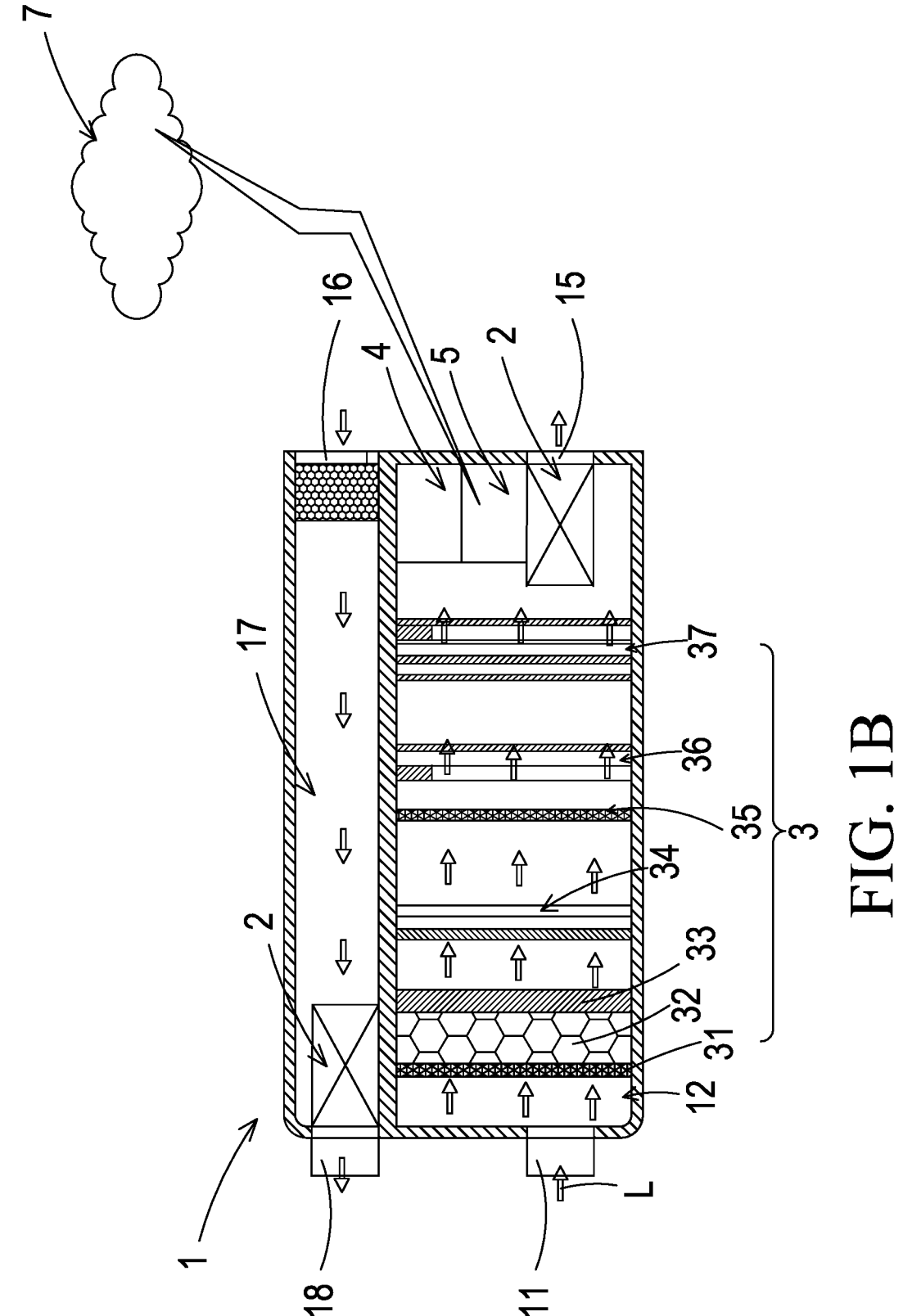
FIG. 1B illustrates a schematic view showing a cloud processing system connected to the fresh air ventilation device of the exemplary embodiment in the present disclosure.

Please refer to FIG. 1A and FIG. 1B, according to one or some embodiments of the present disclosure, a fresh air ventilation device for air pollution prevention is provided and includes a main body 1, at least one blower 2, a filtering and cleaning assembly 3, at least one gas detection module 4, and a micro-controller 5. The at least one blower 2 is disposed in the main body 1 to guide the air convection and to form a flow-guiding path L. The filtering and cleaning assembly 3 is disposed in the flow-guiding path L to filter and clean an air pollution source in the air convection guided by the at least one blower 2. The at least one gas detection module 4 is disposed in the flow-guiding path L of the main body 1 to detect the air pollution source and transmit a gas detection data. The micro-controller 5 wirelessly receives the gas detection data of the at least one gas detection module 4 and performs an intelligent comparison under a surveillance condition so as to transmit a driving command to enable the at least one blower 2 and adjust an air volume of the at least one blower 2. In one aspect of the present disclosure, the surveillance condition is defined as the gas detection data of the air pollution source detected by the at least one gas detection module 4 exceeding a safety detection value.

It is noted that, the blower 2 may be an armature-type blower 2 or a centrifugal-type blower 2, but not limited thereto. Any blower can be an extension of the embodiments of the present disclosure as long as the blower can generate air flow. Moreover, it is noted that the filtering and cleaning assembly 3 is placed before the gas detection module 4 in this embodiment. Additionally, it is noted that, after the micro-controller 5 wirelessly receives the gas detection data detected by the gas detection module 4, the micro-controller 5 performs an intelligent comparison and transmits the driving command to enable the at least one blower 2 or adjust the air volume of the at least 20 one blower 2. Therefore, when the gas detection data is much larger than the safety detection value, the micro-controller 5 adjusts the air volume of the at least one blower 2 to be much larger; while when gas detection data is much closer to the safety detection value, the micro-controller 5 adjusts the air volume of the at least on blower 2 to be much smaller.

Figure 2:
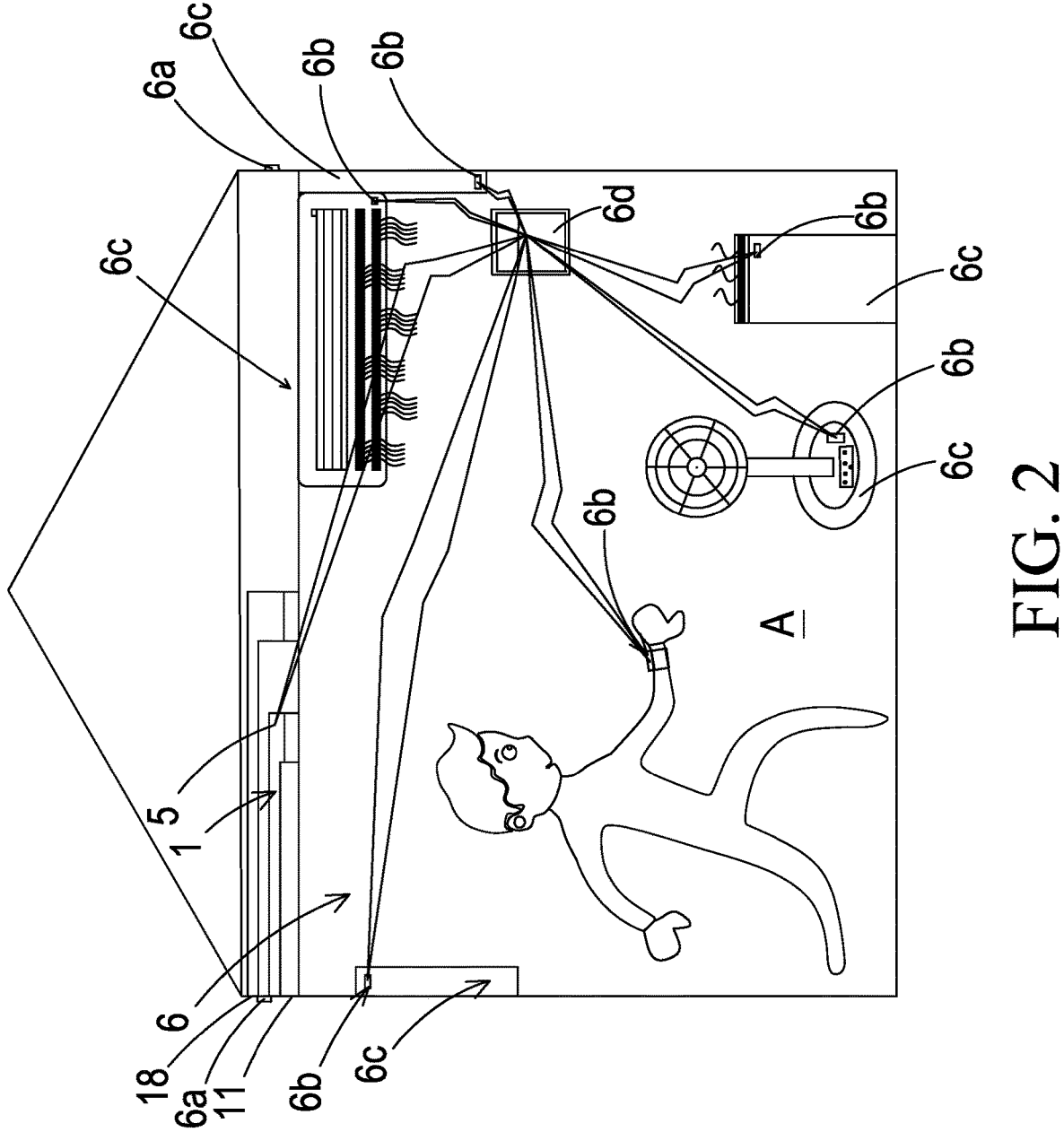
FIG. 2 illustrates a schematic view of an air pollution processing system utilizing the fresh air ventilation device of the exemplary embodiment in the present disclosure.
Figure 3:
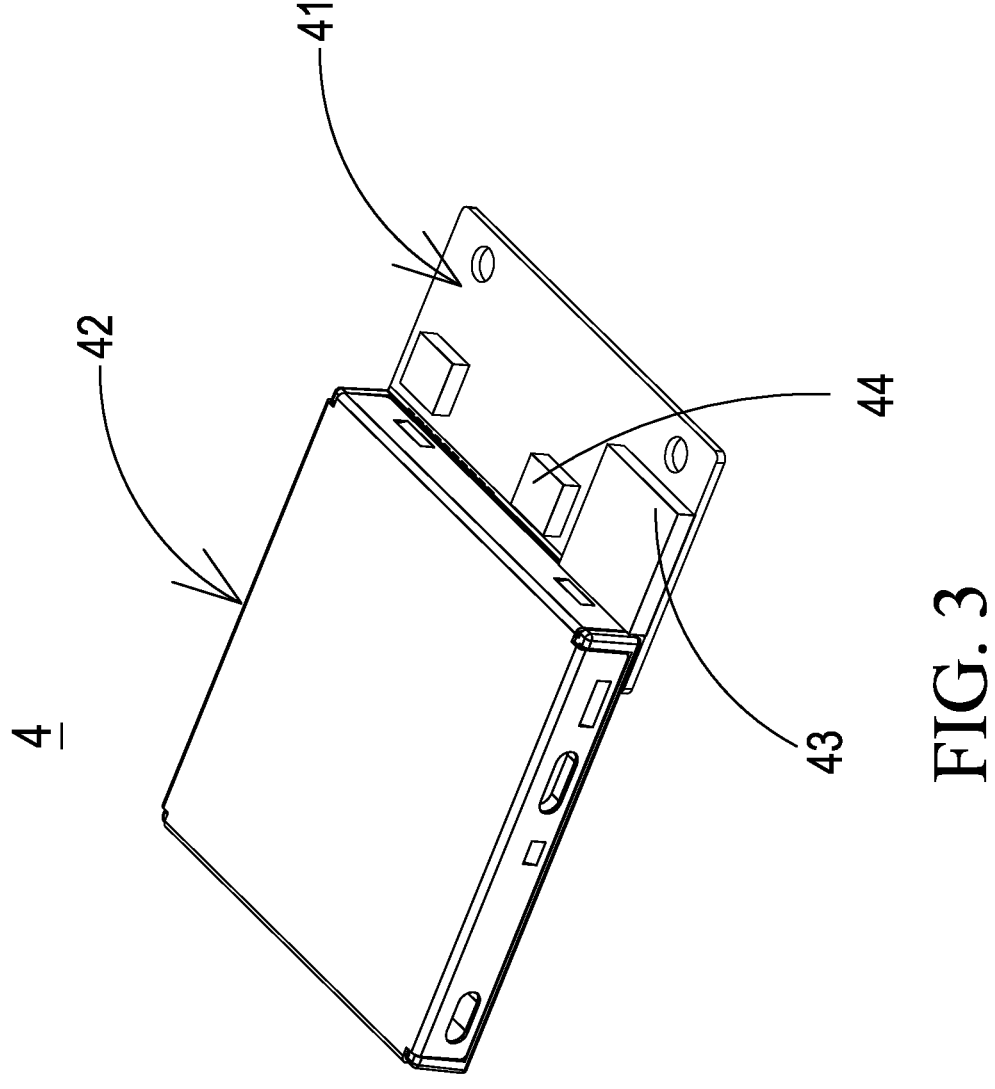
FIG. 3 illustrates a schematic perspective view of a gas detection module of the fresh air ventilation device of the exemplary embodiment in the present disclosure.
Figure 4A:
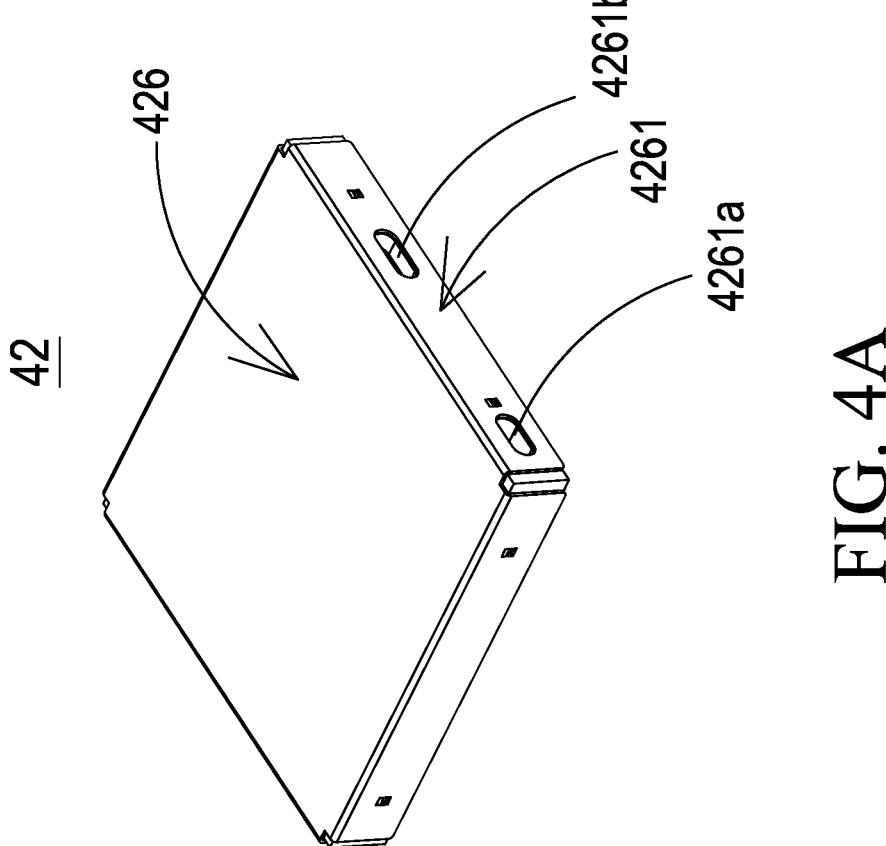
FIG. 4A illustrates a schematic perspective view of a gas detection main body of the gas detection module of the exemplary embodiment in the present disclosure.
Figure 4B:
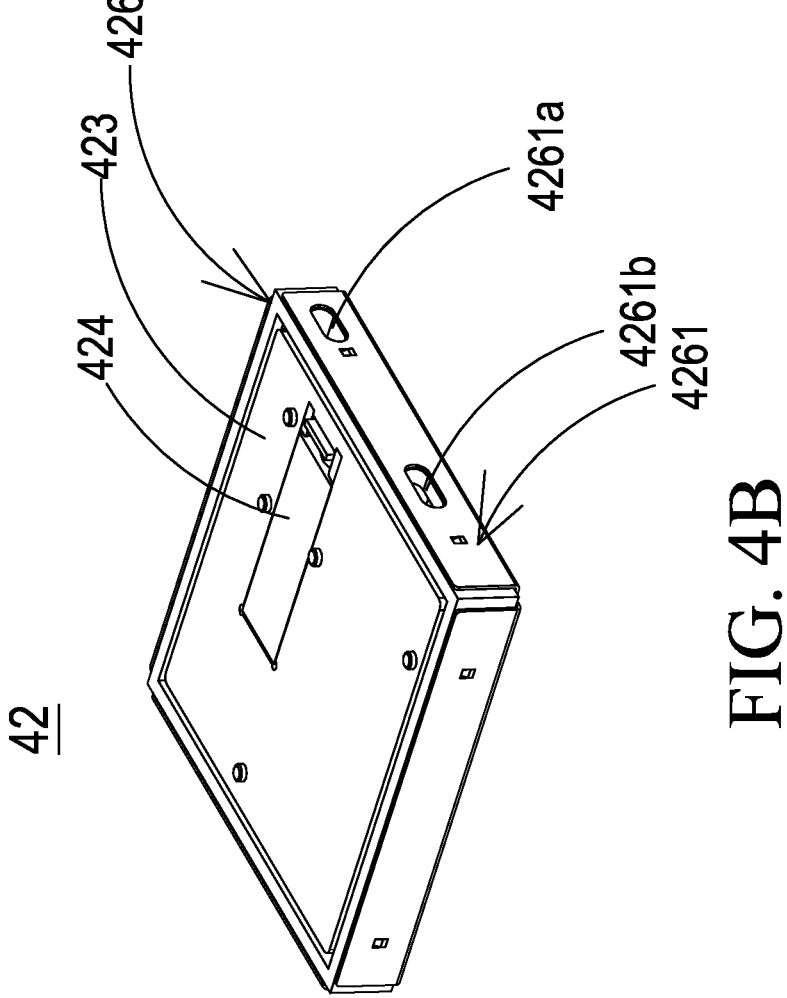
FIG. 4B illustrates a schematic perspective view of the gas detection main body of the gas detection module of the exemplary embodiment in the present disclosure from another view angle.
Figure 4C:
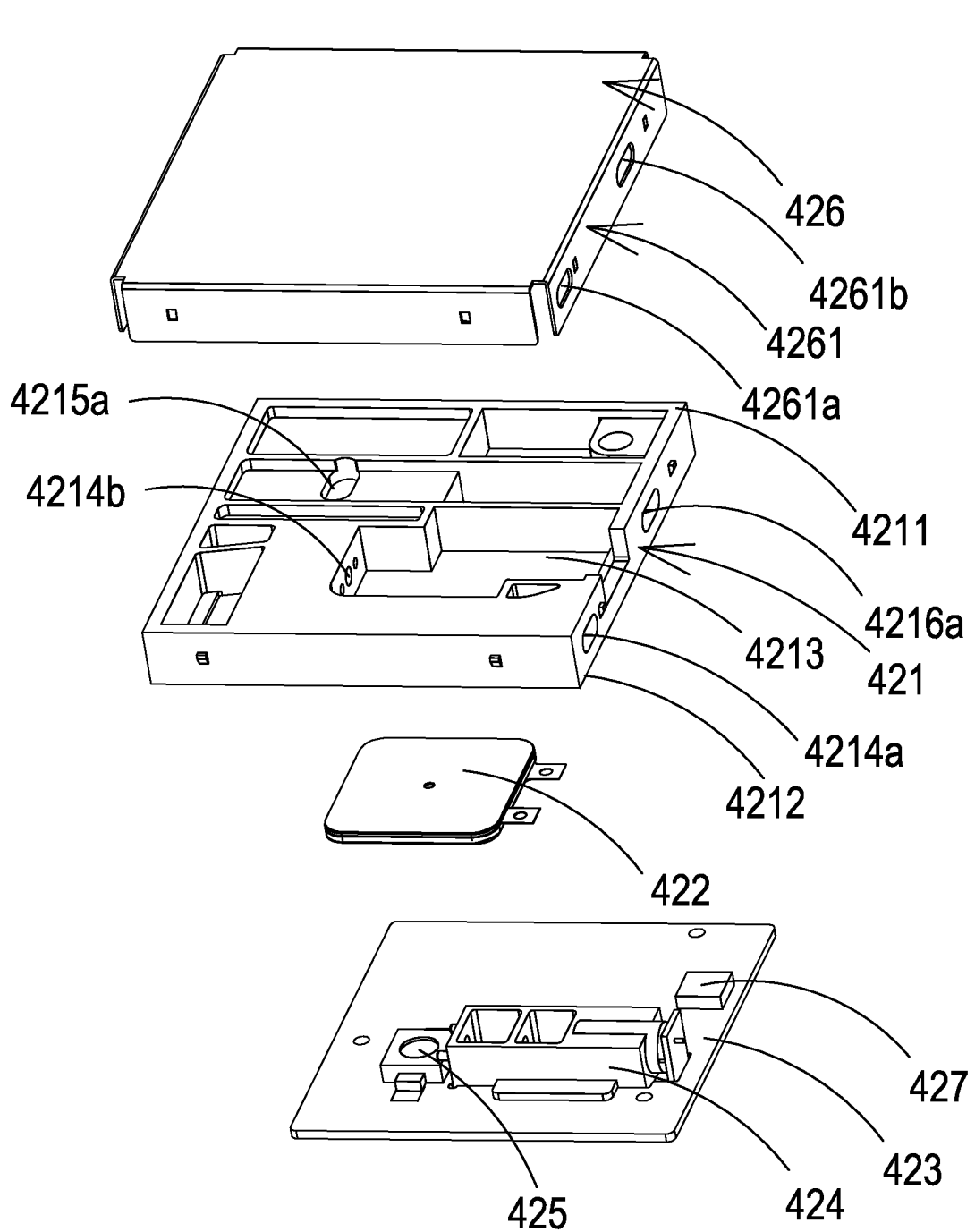
FIG. 4C illustrates an exploded view of the gas detection main body of the gas detection module of the exemplary embodiment in the present disclosure.
Figure 5A:
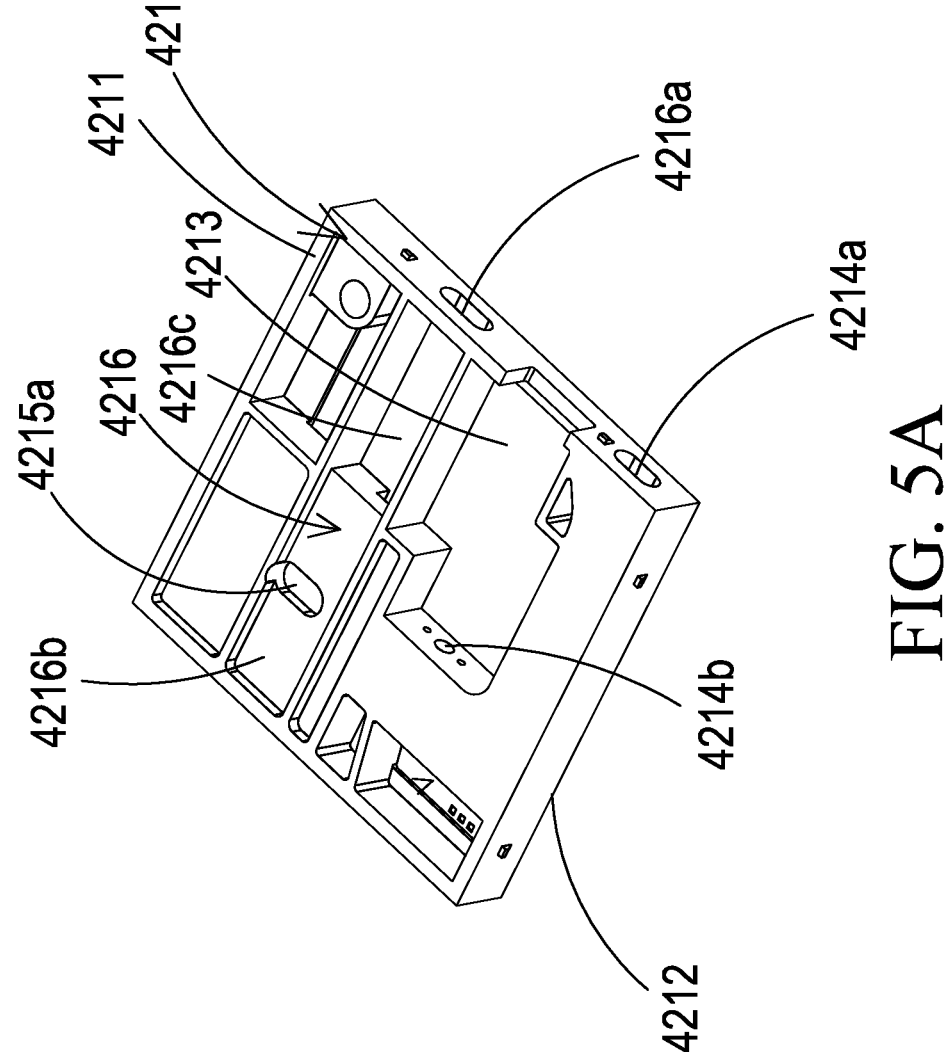
FIG. 5A illustrates a perspective view of a base of the gas detection main body of the gas detection module the exemplary embodiment in the present disclosure.
Figure 5B:
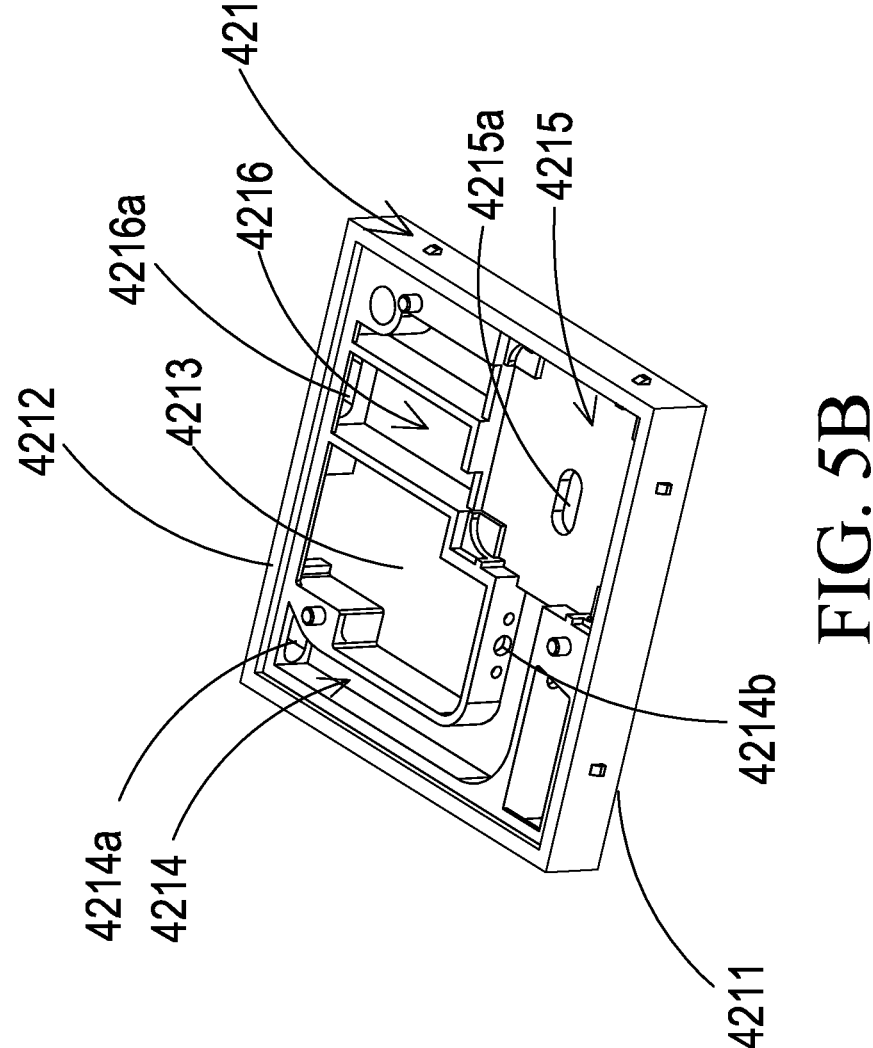
FIG. 5B illustrates a perspective view of the base of the gas detection main body of the gas detection module of the exemplary embodiment in the present disclosure from another view angle.
Figure 6:
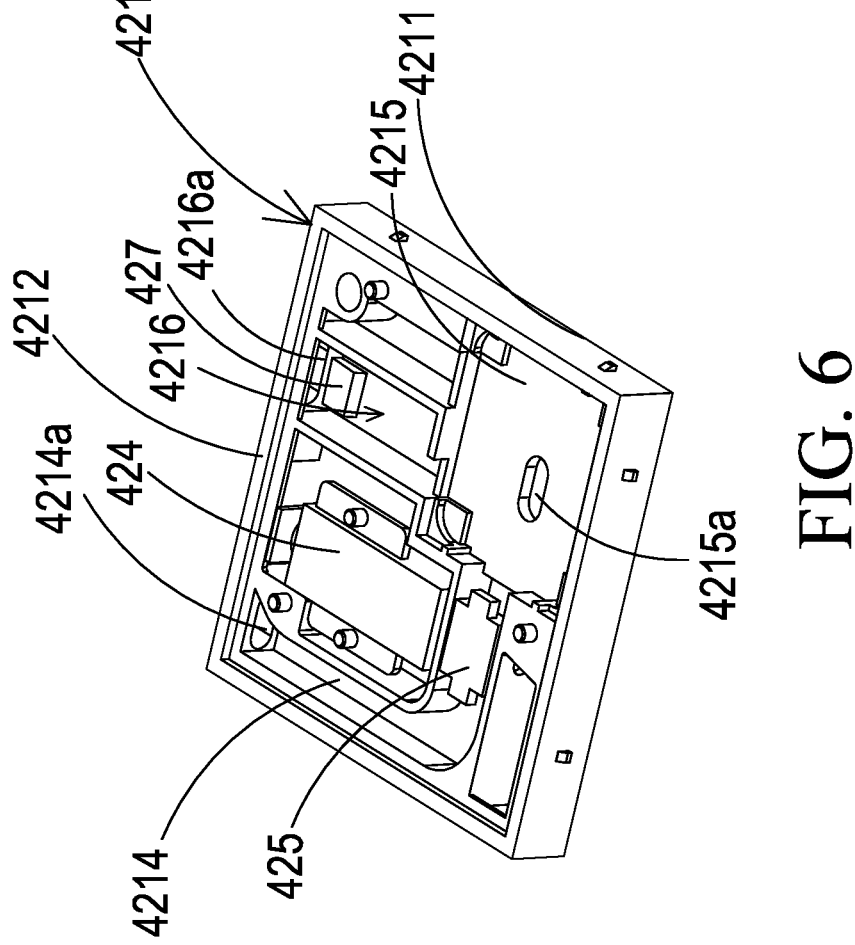
FIG. 6 illustrates a perspective view of the base of the gas detection main body of the gas detection module in combination with a laser component of the gas detection module of the exemplary embodiment in the present disclosure.
Figure 7A:
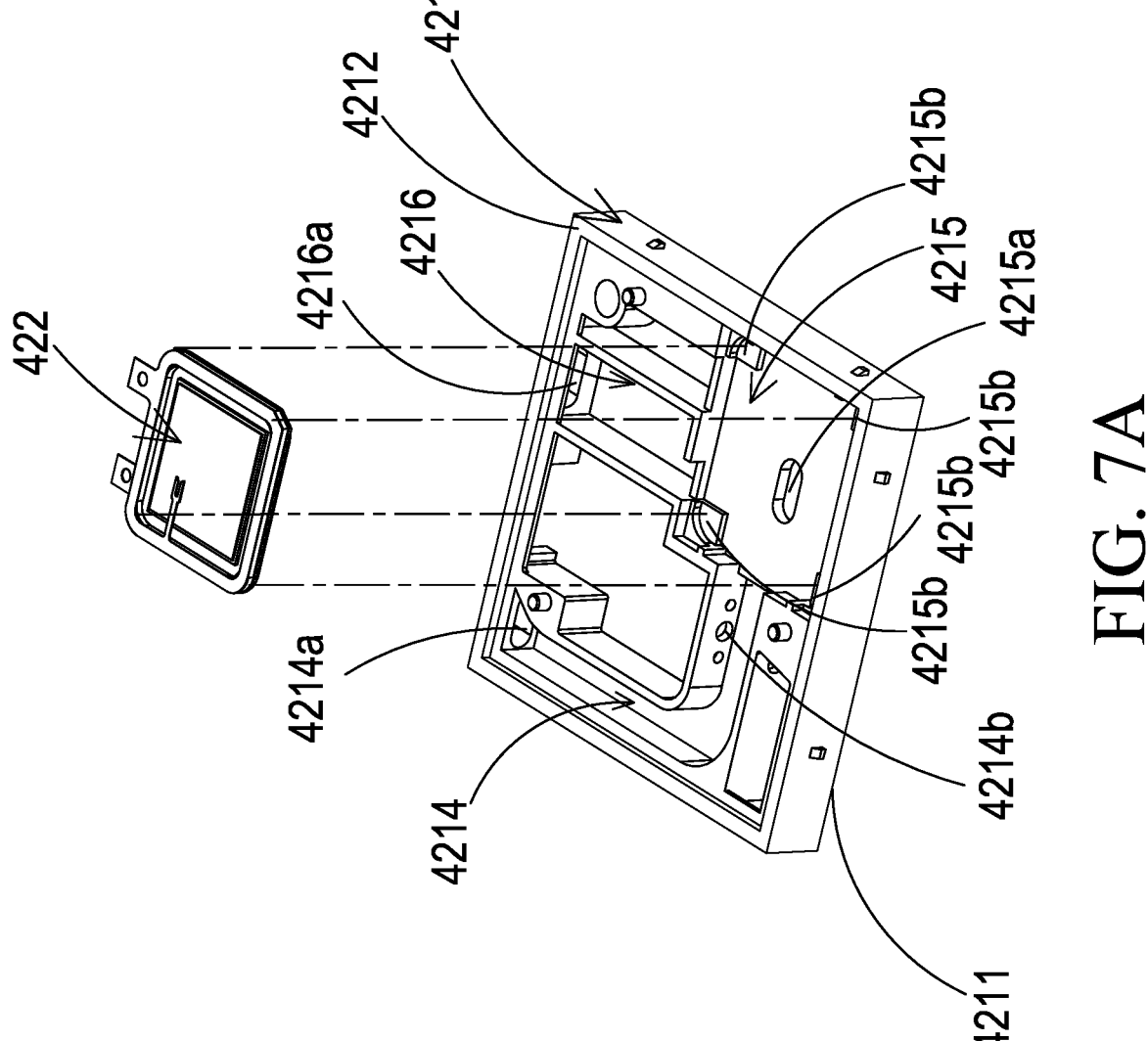
FIG. 7A illustrates an exploded view of a piezoelectric actuator separating from the base of the gas detection main body of the gas detection module of the exemplary embodiment in the present disclosure.
Figure 7B:
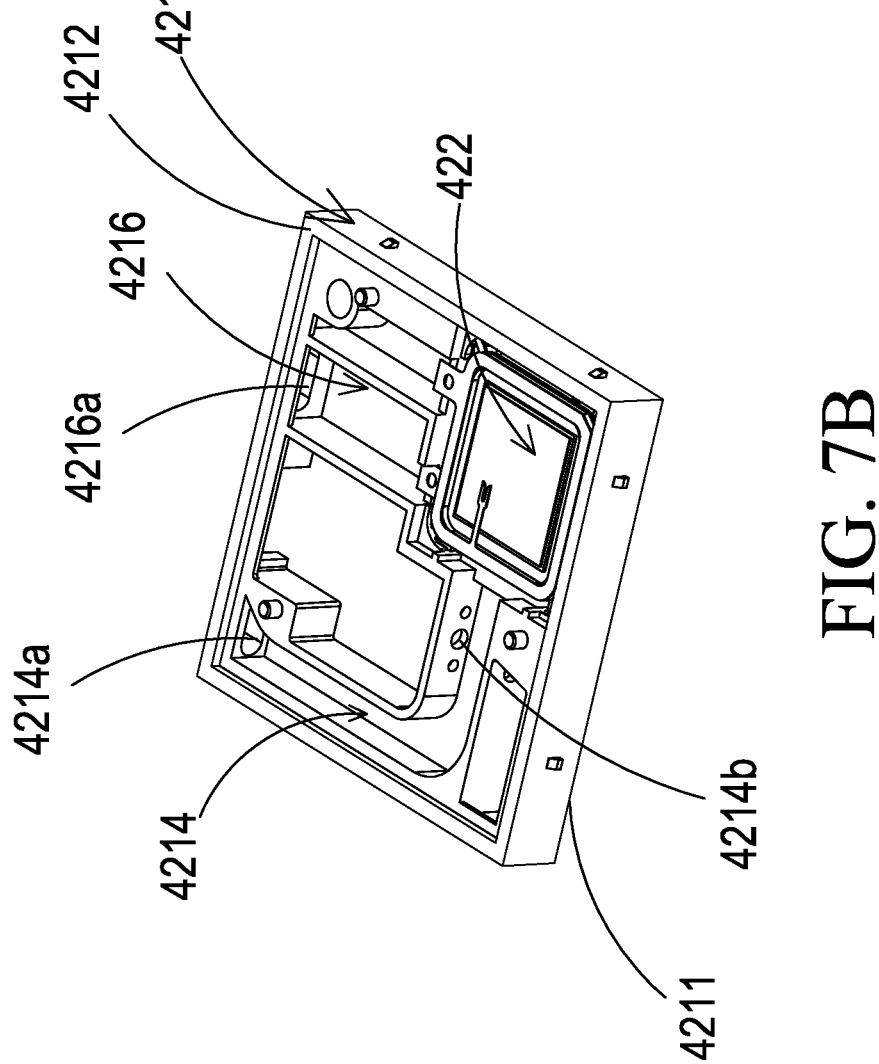
FIG. 7B illustrates a perspective view of the base of the gas detection main body of the gas detection module in combination with a piezoelectric actuator of the gas detection module of the exemplary embodiment in the present disclosure.
Figure 8A:
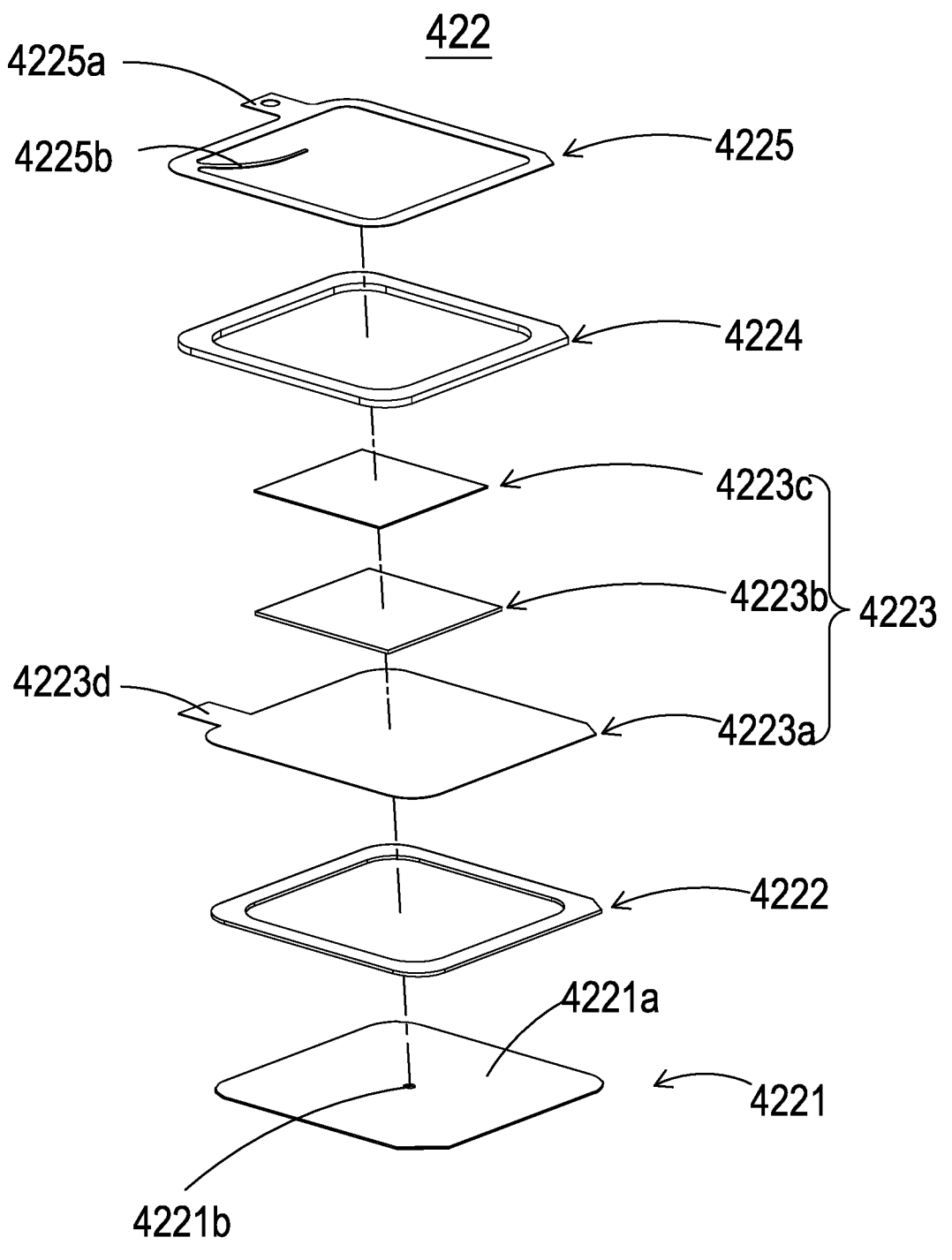
FIG. 8A illustrates an exploded view of the piezoelectric actuator of the gas detection main body of the gas detection module of the exemplary embodiment in the present disclosure.
Figure 8B:
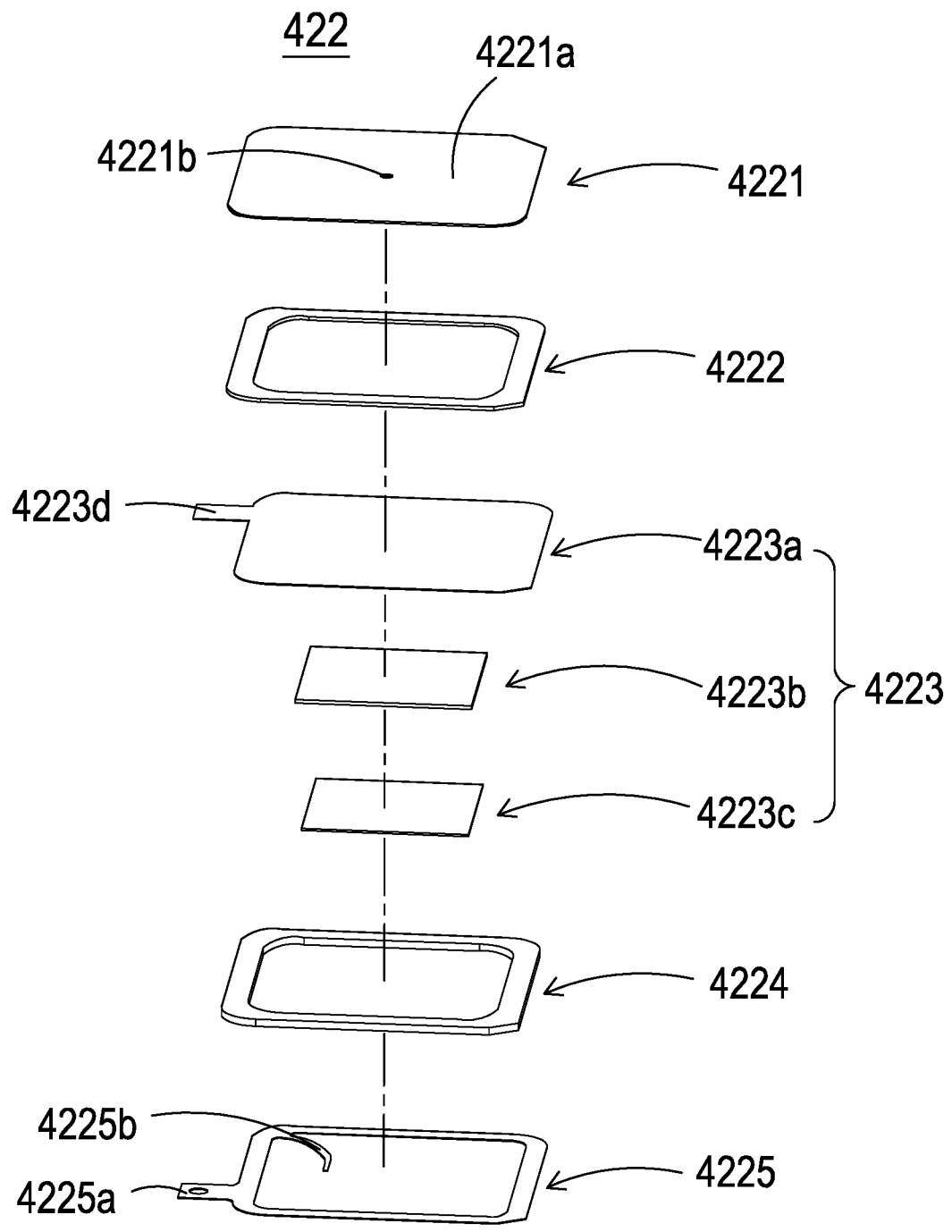
FIG. 8B illustrates an exploded view of the piezoelectric actuator of the gas detection main body of the gas detection module of the exemplary embodiment in the present disclosure from another view angle.

Please refer to FIG. 1A and FIG. 2. The main body 1 comprises at least one gas inlet 11, an inlet channel 12, the filtering and cleaning assembly 3, the at least one blower 2, at least one gas outlet 15, at least one gas-exchange inlet 16, a gas-exchange channel 17, at least one gas-exchange outlet 18, the at least one gas detection module 4, and the micro-controller. The at least one gas inlet 11 is connected to the inlet channel 12. The filtering and cleaning assembly 3 is disposed in the inlet channel 12 for filtering and purifying the gas introduced from the at least one gas inlet 11. The at least one gas outlet 15 is in communication with the inlet channel 12 and is connected to the at least one blower 2 for introducing the filtered and purified gas from the at least one gas outlet 15 into the indoor space A. The at least one gas-exchange inlet 16 is connected to the gas-exchange channel 17, and the gas-exchange channel 17 is in communication with the at least one gas-exchange outlet 18. The micro-controller 5 controls the at least one blower 2. After the micro-controller 5 receives and compares the outdoor gas detection data with the indoor gas detection data, the micro-controller 5 intelligently and selectively controls the introduction of the outdoor gas into the indoor space A, so that the polluted gas in the indoor space A is exchanged with the outdoor gas, thereby allowing the indoor gas detection data of the polluted gas in the indoor space A to be decreased to the safety detection value.

In this embodiment, when the micro-controller 5 receives and compares the indoor gas detection data with the outdoor gas detection data and determines that the outdoor gas detection data is better than the indoor gas detection data, the micro-controller 5 intelligently and selectively controls the introduction of the outdoor gas into the indoor space A, so that the micro-controller 5 intelligently and selectively enables the at least one blower 2 and controls the operation time of the at least one blower 2. Therefore, the at least one blower 2 is enabled to introduce the outdoor gas into the inlet channel 12 from the at least one gas inlet 11, pass through the filtering and cleaning assembly 3 for filtering and purifying, and introduce into the at least one gas outlet 15 to enter the indoor space A, and the polluted gas in the indoor space A is introduced into the gas-exchange channel 17 from the at least one gas-exchange inlet 16 and discharged to the outdoor space B from the at least one gas-exchange outlet 18. Hence, the polluted gas in the indoor space A can be exchanged to the outdoor space B, thereby allowing the indoor gas detection data of the polluted gas in the indoor space A to be decreased to the safety detection value.

As shown in FIG. 3 to FIG. 9A, the gas detection module 4 includes a control circuit board 41, a gas detection main body 42, a microprocessor 43, and a communication device 44. The gas detection main body 42, the microprocessor 43, and the communication device 44 are integrally packaged with the control circuit board 41 and electrically connected to each other. The microprocessor 43 controls the operation of the gas detection main body 42, the gas detection main body 42 detects the air pollution source and outputs a detection signal, and the microprocessor 43 receives the detection signal so as to compute, process, and output the detection signal, therefore the microprocessor 43 of the gas detection module 4 generates the gas detection data and provides the communication device 44 with the gas detection data for transmitting outwardly. Moreover, in some embodiments, the outwardly communication transmission of the communication device 44 may be implemented through a bidirectional wired transmission. For example, the wired transmission may be achieved by a USB port, a mini-USB port, and micro-USB port. Alternatively, in some embodiments, the outwardly communication transmission of the communication devices 44 may also be implemented through a bidirectional wireless transmission. For example, the wireless transmission may be achieved by a Wi-Fi module, a Bluetooth module, a radiofrequency identification module, and a near field communication module. The micro-controller 5 wirelessly receives the gas detection data transmitted by the communication device 44.

Moreover, in one or some embodiments, the gas detection main body 42 includes a base 421, a piezoelectric actuator 422, a driving circuit board 423, a laser component 424, a particulate sensor 425, an outer cover 426, and a gas sensor 427. The base 421 has a first surface 4211, a second surface 4212, a laser installation region 4213, a gas inlet groove 4214, a gas-guiding component installation region 4215, and a gas outlet groove 4216. The first surface 4211 and the second surface 4212 are opposite to each other. The laser installation region 4213 is formed by hollowing out the base 421 from the first surface 4211 to the second surface 4212 for accommodating the laser component 424. The outer cover 426 covers the base 421 and has a side plate 4261. The side plate 4261 has a gas inlet opening 4261a and a gas outlet opening 4261b. The gas inlet groove 4214 is recessed from the second surface 4212 and located adjacent to the laser installation region 4213. The gas inlet groove 4214 has a gas inlet through hole 4214a and two lateral walls. The gas inlet through hole 4214a is in communication with the outside environment of the base 421 and is corresponding to the gas inlet opening 4261a of the outer cover 426. Two light penetration windows 4214b penetrate the two lateral walls of the gas inlet groove 4214 and are in communication with the laser installation region 4213. Therefore, when the first surface 4211 of the base 421 is covered by the outer cover 426, and the second surface 4212 of the base 421 is covered by the driving circuit board 423, a gas inlet path can be defined by the gas inlet groove 4214.

The gas-guiding component installation region 4215 is recessed from the second surface 4212 and in communication with the gas inlet groove 4214. A ventilation hole 4215a penetrates a bottom surface of the gas-guiding component installation region 4215. Each of the four corners of the gas-guiding component installation region 4215 has a positioning bump 4215b. The gas outlet groove 4216 has a gas outlet through hole 4216a, and the gas outlet through hole 4216a is corresponding to the gas outlet opening 4261b of the outer cover 426. The gas outlet groove 4216 includes a first region 4216b and a second region 4216c. The first region 4216b is recessed from a portion of the first surface 4211 corresponding to a vertical projection region of the gas-guiding component installation region 4215. The second region 4216c is at a portion extending from a region that is not corresponding to the vertical projection region of the gas-guiding component installation region 4215, and the second region 4216c is hollowed out from the first surface 4211 to the second surface 4212. The first region 4216b is connected to the second region 4216c to form a stepped structure. Moreover, the first region 4216b of the gas outlet groove 4216 is in communication with the ventilation hole 4215a of the gas-guiding component installation region 4215, and the second region 4216c of the gas outlet groove 4216 is in communication with the gas outlet through hole 4216a. Therefore, when the first surface 4211 of the base 421 is covered by the outer cover 426 and the second surface 4212 of the base 421 is covered by the driving circuit board 423, a gas outlet path can be defined by the gas outlet groove 4216 and the driving circuit board 423.

Furthermore, the laser component 424 and the particulate sensor 425 are disposed on the driving circuit board 423 and located in the base 421. The laser component 424 and the particulate sensor 425 are electrically connected to the driving circuit board 423. It should notice that the driving circuit board 423 is omitted to clearly explain the positions of the laser component 424, the particulate sensor 425, and the base 421. In the embodiment of the present disclosure, the laser component 424 is located at the laser installation region 4213 of the base 421. The particulate sensor 425 is located at the gas inlet groove 4214 of the base 421 and aligned with the laser component 424. Moreover, the laser component 424 is corresponding to the light penetration windows 4214b so as to allow the light beam emitted by the laser component 424 to pass therethrough and into the gas inlet groove 4214. The light path of the light beam emitted by the laser component 424 passes through the light penetration windows 4214b and is orthogonal to the gas inlet groove 4214. The light beam emitted by the laser component 424 passes into the gas inlet groove 4214 through the light penetration windows 4214b, thereby the particulate matters in the gas inlet groove 4214 is illuminated by the light beam. When the light beam illuminates on the particulate matters, the light beam will be scattered and generate light spots. Hence, the light spots generated by the scattering are received and calculated by the particulate sensor 425 located at the position orthogonal to the gas inlet groove 4214 to obtain the detection data of the gas. Furthermore, the gas sensor 427 is disposed on the driving circuit board 423 and is located at the gas outlet groove 4216 for detecting the polluted gas introduced into the gas outlet groove 4216, and the gas sensor 427 is electrically connected to the driving circuit board 423. In one embodiment of the present disclosure, the particulate sensor 425 is provided for detecting the information of particulate matters, and the gas sensor 427 includes at least one selected from the group consisting of a volatile organic compound detector capable of detecting gas information of carbon dioxide ($CO_2$) or total volatile organic compounds (TVOC), a formaldehyde sensor capable of detecting gas information of formaldehyde (HCHO) gas, a bacterial sensor capable of detecting information of bacteria or fungi, and a virus sensor capable of detecting information of viruses, a temperature and humidity sensor capable of detecting the temperature and humidity of the gas, and any combination thereof.

Moreover, the piezoelectric actuator 422 is located at the gas-guiding component installation region 4215 with square-shaped of the base 421, and the gas-guiding component installation region 4215 is in communication with the gas inlet groove 4214. When the piezoelectric actuator 422 is enabled, the gas in the gas inlet groove 4214 is inhaled into the piezoelectric actuator 422, passing through the ventilation hole 4215a of the gas-guiding component installation region 4215, and entering the gas outlet groove 4216. Moreover, the driving circuit board 423 covers the second surface 4212 of the base 421. The laser component 424 and the particulate sensor 425 are disposed on the driving circuit board 423 and electrically connected to the driving circuit board 423. As the outer cover 426 covers the base 421, the gas inlet opening 4261a is corresponding to the gas inlet through hole 4214a of the base 421, and the gas outlet opening 4216b is corresponding to the gas outlet through hole 4216a of the base 421.

Furthermore, the piezoelectric actuator 422 includes a nozzle plate 4221, a chamber frame 4222, an actuation body 4223, an insulation frame 4224, and a conductive frame 4225. The nozzle plate 4221 is made by a flexible material and has a suspension sheet 4221a and a hollow hole 4221b. The suspension sheet 4221a is a flexible sheet which can bend and vibrate. The shape and the size of the suspension sheet 4221a approximately corresponding to the inner edge of the gas-guiding component installation region 4215. The hollow hole 4221b penetrates through the center portion of the suspension sheet 4221a for the gas flowing therethrough. In one embodiment of the present disclosure, the shape of the suspension sheet 4221a can be selected from square, circle, ellipse, triangle, or polygon.

Furthermore, the chamber frame 4222 is stacked on the nozzle plate 4221, and the shape of the chamber frame 4222 is corresponding to the shape of the nozzle plate 4221. The actuation body 4223 is stacked on the chamber frame 4222. A resonance chamber 4226 is collectively defined between the actuation body 4223, the nozzle plate 4221, and the suspension sheet 4221a. The insulation frame 4224 is stacked on the actuation body 4223. The appearance of the insulation frame 4224 is similar to the appearance of the nozzle plate 4221. The conductive frame 4225 is stacked on the insulation frame 4224. The appearance of the conductive frame 4225 is similar to the appearance of the insulation frame 4224. The conductive frame 4225 has a conductive pin 4225a and a conductive electrode 4225b. The conductive pin 4225a extends outwardly from the outer edge of the conductive frame 4225, and the conductive electrode 4225b extends inwardly from the inner edge of the conductive frame 4225.

Moreover, the actuation body 4223 further includes a piezoelectric carrying plate 4223a, an adjusting resonance plate 4223b, and a piezoelectric plate 4223c. The piezoelectric carrying plate 4223a is stacked on the chamber frame 4222, and the adjusting resonance plate 4223b is stacked on the piezoelectric carrying plate 4223a. The piezoelectric plate 4223c is stacked on the adjusting resonance plate 4223b. The adjusting resonance plate 4223b and the piezoelectric plate 4223c are accommodated in the insulation frame 4224. The conductive electrode 4225b of the conductive frame 4225 is electrically connected to the piezoelectric plate 4223c. In one preferred embodiment of the present disclosure, the piezoelectric carrying plate 4223a and the adjusting resonance plate 4223b are both made of conductive material(s). The piezoelectric carrying plate 4223a has a piezoelectric pin 4223d. The piezoelectric pin 4223d and the conductive pin 4225a are in electrical connection with a driving circuit (not shown) of the driving circuit board 423 to receive a driving signal (which may be a driving frequency and a driving voltage). The piezoelectric pin 4223d, the piezoelectric carrying plate 4223a, the adjusting resonance plate 4223b, the piezoelectric plate 4223c, the conductive electrode 4225b, the conductive frame 4225, and the conductive pin 4225a may together generate an electrical circuit for transmitting the driving signal, and the insulation frame 4224 is provided for electrically insulating the conductive frame 4225 from the actuation body 4223 to avoid short circuit, thereby the driving signal can be transmitted to the piezoelectric plate 4223c. When the piezoelectric plate 4223c receives the driving signal, the piezoelectric plate 4223c deforms owing to the piezoelectric effect, and thus the piezoelectric carrying plate 4223a and the adjusting resonance plate 4223b are driven to vibrate reciprocatingly.

Moreover, the adjusting resonance plate 4223b is disposed between the piezoelectric plate 4223c and the piezoelectric carrying plate 4223a as a cushion element so as to adjust the vibration frequency of the piezoelectric carrying plate 4223a. Generally, the thickness of the adjusting resonance plate 4223b is greater than the thickness of the piezoelectric carrying plate 4223a. The thickness of the adjusting resonance plate 4223b may be modified to adjust the vibration frequency of the actuation body 4223. The nozzle plate 4221, the chamber frame 4222, the actuation body 4223, the insulation frame 4224, and the conductive frame 4225 are sequentially stacked and assembled and are positioned in the gas-guiding component installation region 4215, thereby a clearance 4221c is defined between the suspension sheet 4221a and the inner edge of the gas-guiding component installation region 4215 for the gas to pass therethrough.

A gas flow chamber 4227 is formed between the nozzle plate 4221 and the bottom surface of the gas-guiding component installation region 4215. The gas flow chamber 4227 is in communication with the resonance chamber 4226 formed between the actuation body 4223, the chamber frame 4222, and the suspension sheet 4221a through the hollow hole 4221b of the nozzle plate 4221. In one aspect of the present invention, the resonance chamber 4226 and the suspension sheet 4221a can generate the Helmholtz resonance effect to improve the transmission efficiency of the gas through controlling the vibration frequency of the gas in the resonance chamber 4226 to be close to the vibration frequency of the suspension sheet 4221a. When the piezoelectric plate 4223c moves in a direction away from the bottom surface of the gas-guiding component installation region 4215, the piezoelectric plate 4223c drives the suspension sheet 4221a of the nozzle plate 4221 to move in the direction away from the bottom surface of the gas-guiding component installation region 4215 correspondingly. Hence, the volume of the gas flow chamber 4227 expands dramatically, therefore the internal pressure of the gas flow chamber 4227 decreases and creates a negative pressure, drawing the gas outside the piezoelectric actuator 422 to flow into the piezoelectric actuator 422 through the clearance 4221c and enter the resonance chamber 4226 through the hollow hole 4221b, thereby increasing the gas pressure of the resonance chamber 4226 and thus generating a pressure gradient. When the piezoelectric plate 4223c drives the suspension sheet 4221a of the nozzle plate 4221 to move toward the bottom surface of the gas-guiding component installation region 4215, the gas inside the resonance chamber 4226 is pushed to flow out quickly through the hollow hole 4221b to further push the gas inside the gas flow chamber 4227, thereby the converged gas can be quickly and massively ejected out of the gas flow chamber 4227 through the ventilation hole 4215*a* of the gas-guiding component installation region 4215 in a state closing to an ideal gas state under the Benulli's law.

Figure 9A:
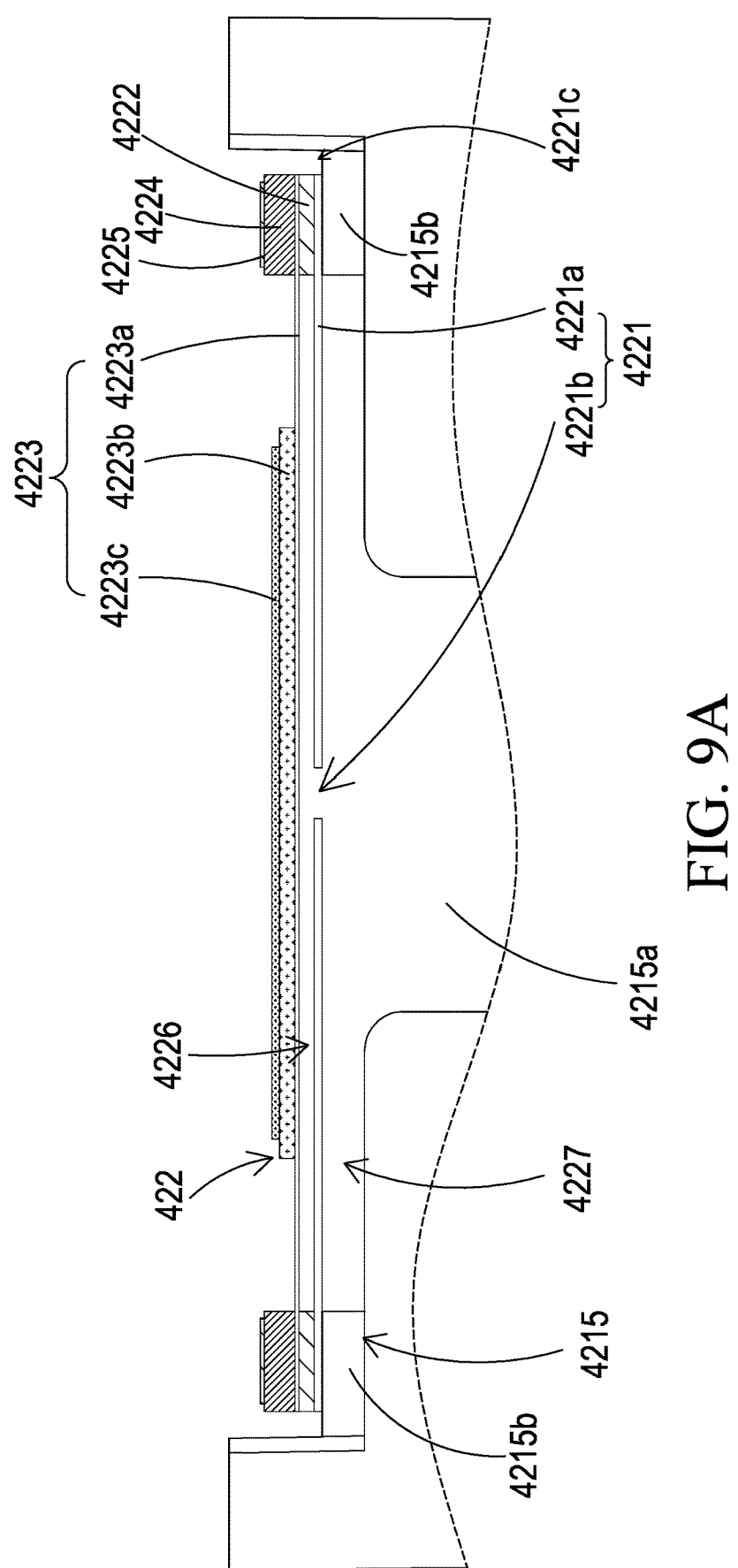
FIG. 9A illustrates a cross-sectional view of the piezoelectric actuator of the gas detection main body of the gas detection module of the exemplary embodiment in the present disclosure.
Figure 9B:
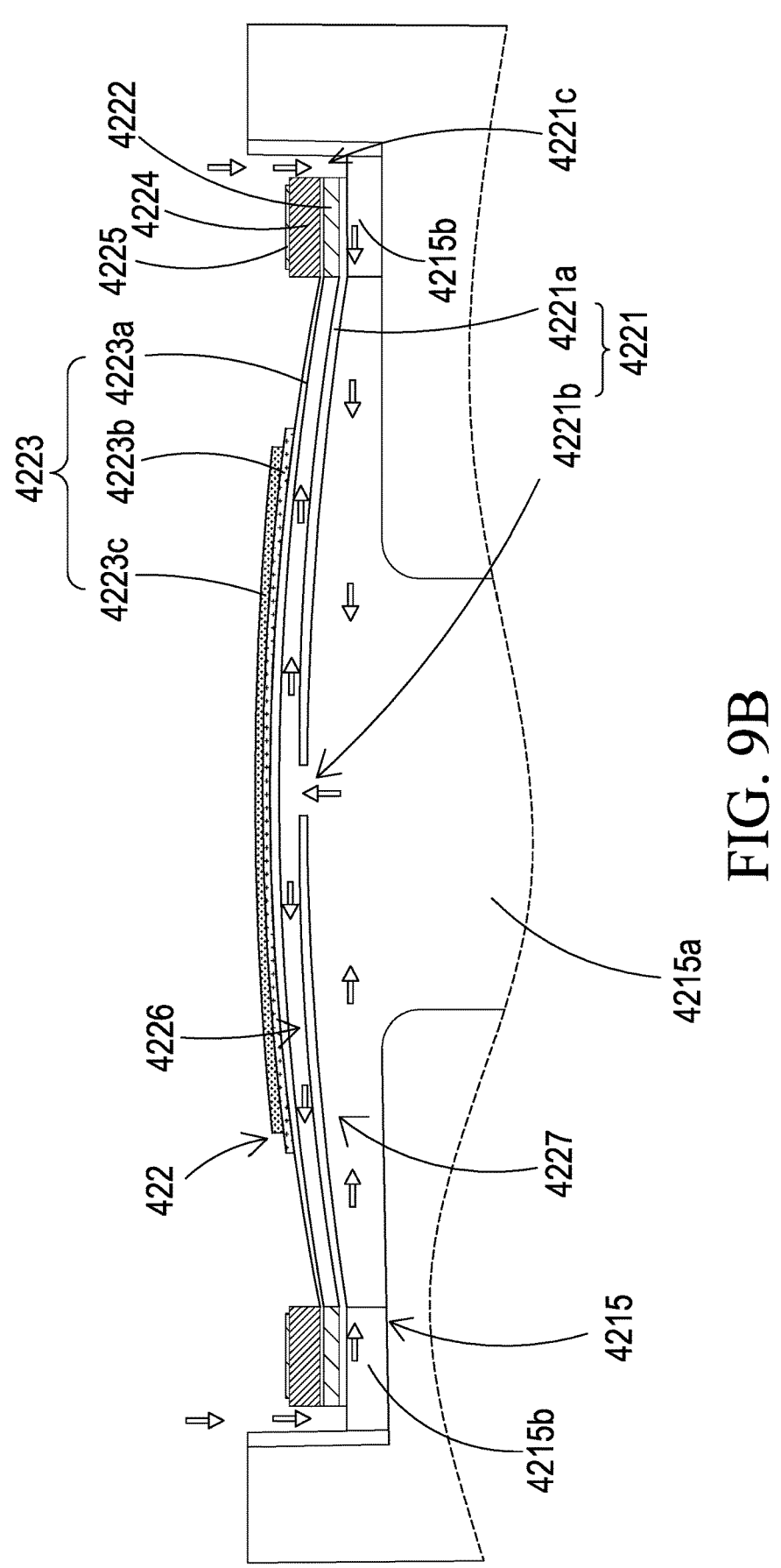
FIG. 9B illustrates a cross-sectional view showing the operation step (1) of the piezoelectric actuator of the gas detection main body of the gas detection module of the exemplary embodiment in the present disclosure.
Figure 9C:
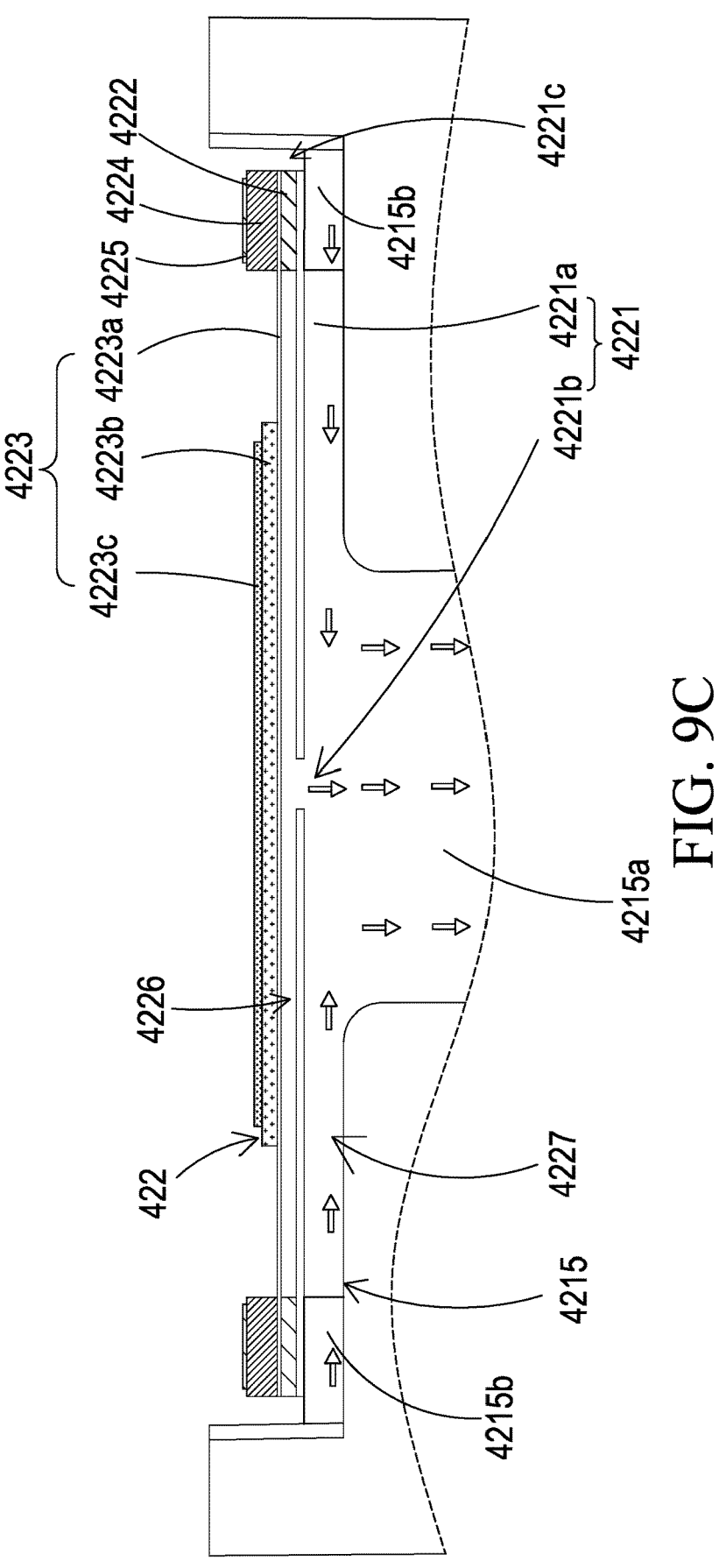
FIG. 9C illustrates a cross-sectional view showing the operation step (2) of the piezoelectric actuator of the gas detection main body of the gas detection module of the exemplary embodiment in the present disclosure.

Therefore, through repeating the steps as shown in FIG. 9B and FIG. 9C, the piezoelectric plate 4223*c* can bend and vibrate reciprocatingly. Further, after the gas is discharged out of the resonance chamber 4226, the internal pressure of the resonance chamber 4226 is lower than the equilibrium pressure due to the inertia, as a result, the pressure difference guides the gas outside the resonance chamber 4226 into the resonance chamber 4226 again. Therefore, through controlling the vibration frequency of the gas in the resonance chamber 4226 to be close to the vibration frequency of the piezoelectric plate 4223*c*, the resonance chamber 4226 and the piezoelectric plate 4223*c* can generate the Helmholtz resonance effect so as to achieve effective, high-speed, and large-volume gas transmission of the gas.

Figure 10A:
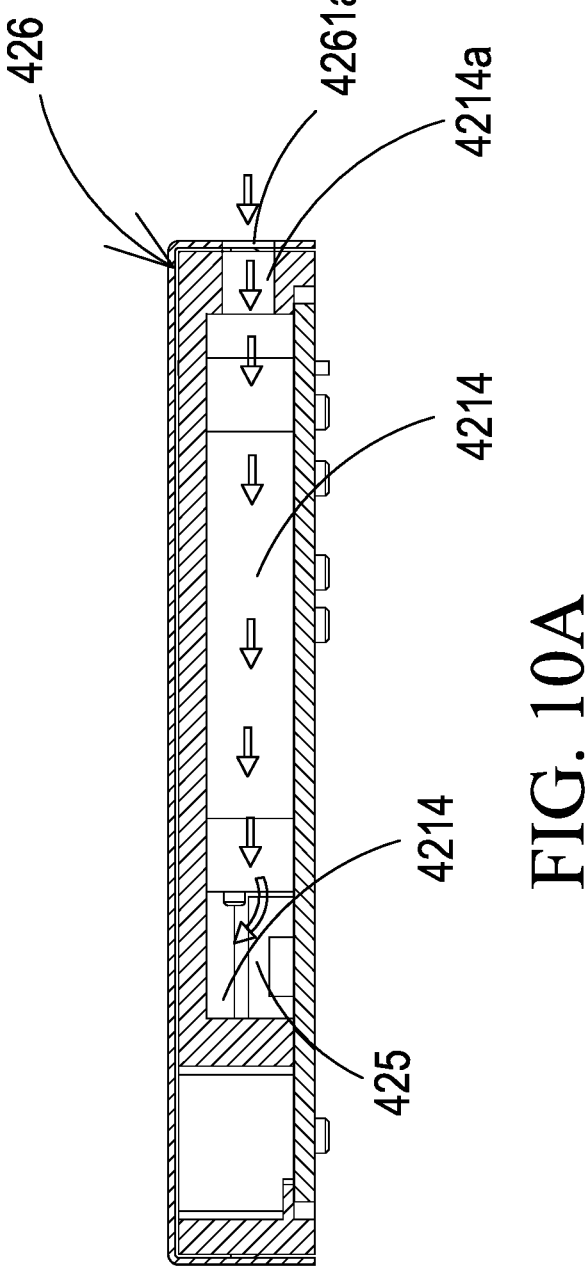
FIG. 10A illustrates a schematic cross-sectional view showing the introduction of gas into the gas detection main body of the gas detection module of the exemplary embodiment in the present disclosure.
Figure 10B:
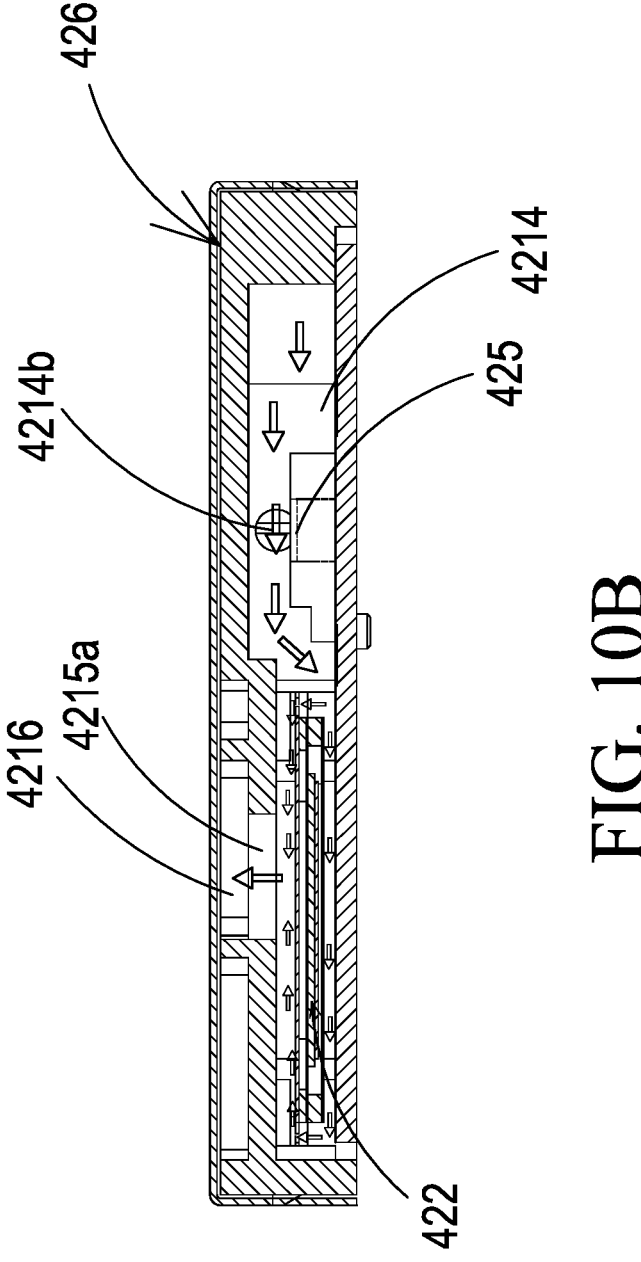
FIG. 10B illustrates a schematic cross-sectional view showing the gas detection of the gas detection main body of the gas detection module of the exemplary embodiment in the present disclosure.
Figure 10C:
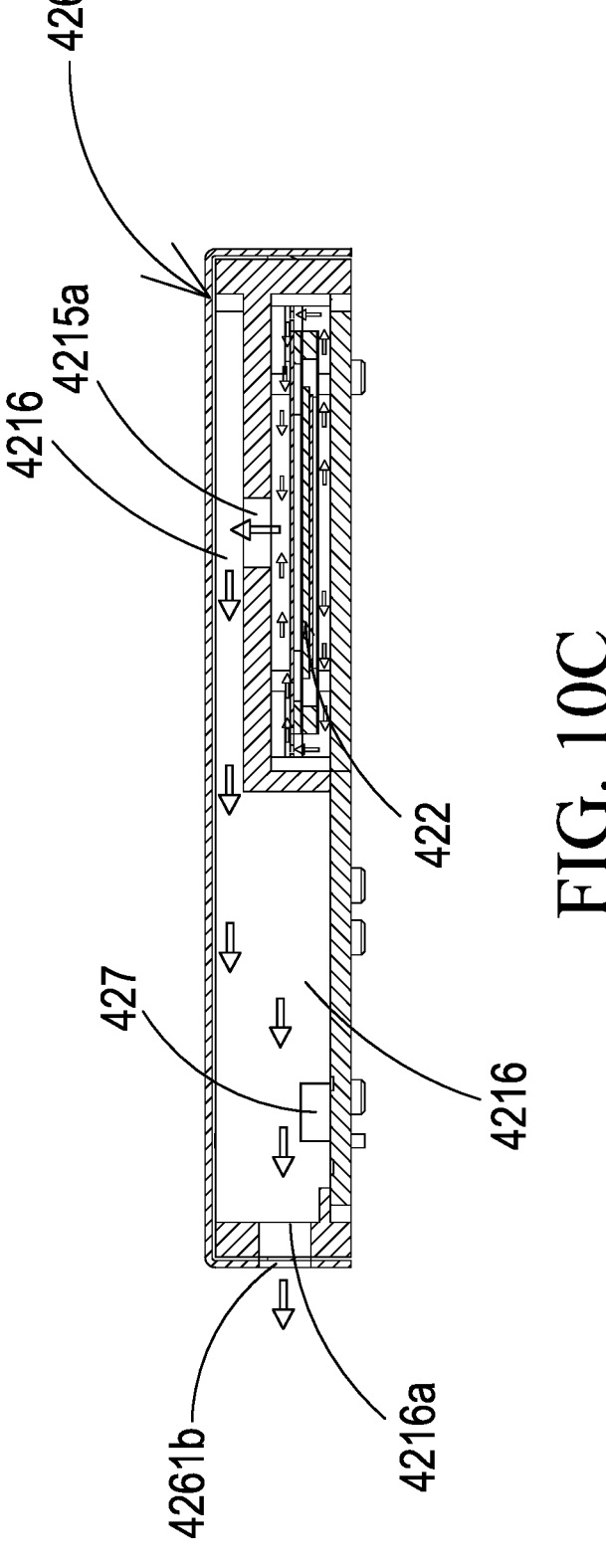
FIG. 10C illustrates a schematic cross-sectional view showing the discharging of gas out of the gas detection main body of the gas detection module of the exemplary embodiment in the present disclosure.

Moreover, as shown in FIG. 10A to FIG. 10C, the gas enters the gas detection main body 42 from the gas inlet opening 4261*a* of the outer cover 426, flows into the gas inlet groove 4214 of the base 421 through the gas inlet through hole 4214*a*, and reaches the position of the particulate sensor 425. Furthermore, the piezoelectric actuator 122 continuously drives the gas into the gas inlet path so as to facilitate the gas inside the detection main body 42 to stably and quickly pass through the particulate sensor 425. Next, the light beam emitted by the laser component 424 passes through the light penetration windows 4214*b*, enters the gas inlet groove 4214, and illuminates the gas in the gas inlet groove 4214 which passes through the particulate sensor 425. When the light beam illuminates on the particulate matters in the gas, the light beam will be scattered and generate light spots. The particulate sensor 425 receives and calculates the light spots generated by the scattering to obtain the information of the particulate matters in the gas such as the particle size and the number of the particulate matters. Moreover, the gas passing through the particulate sensor 425 is continuously introduced into the ventilation hole 4215*a* of the gas-guiding component installation region 4215 by the piezoelectric actuator 422 and enters the gas outlet groove 4216. Finally, after the gas enters the gas outlet groove 4216, since the piezoelectric actuator 422 continuously delivers the gas into gas outlet groove 4216, therefore the gas is continuously pushed and discharged out of the gas detection main body 42 through the gas outlet through hole 4216*a* and the gas outlet opening 4261*b*.

Please refer to FIG. 1A and FIG. 1B. The filtering and cleaning assembly 3 may be the combination of various embodiments. In one embodiment, the filtering and cleaning assembly 3 may be an activated carbon 31, or a high-efficiency particulate air (HEPA) filter 32, or a combination of the activated carbon 31, the high-efficiency particulate air filter 32, and a zeolite mesh 33. In some embodiments, a cleansing factor layer having chlorine dioxide may be coated on the activated carbon 31 or the high-efficiency particulate air filter 32 for suppressing viruses, bacteria, fungus, influenza A virus, influenza B virus, Enterovirus, and Norovirus in the polluted gas introduced into the filtering and cleaning assembly 3. Accordingly, the suppressing rate may exceed 99%, allowing the reduction of the cross infections of the viruses. In some other embodiments, a herbal protection coating layer including the extracts of *Rhus chinensis* Mill (may be *Rhus chinensis* Mill from Japan) and the extracts of *Ginkgo biloba* may be coated on the activated carbon 31 or the high-efficiency particulate air filter 32 to generate a herbal protection anti-allergy filter which can efficiently perform anti-allergy function and destroy cell surface proteins of influenza viruses (e.g., influenza virus subtype H1N1) passing through the herbal protection anti-allergy filter. Alternatively, in some other embodiments, a layer of silver ions may be coated on the activated carbon 31 or the high-efficiency particulate air filter 32 for suppressing viruses, bacteria, and fungus in the polluted gas introduced into the filtering and cleaning assembly 3.

The activated carbon 31 is provided for filtering and absorbing PM2.5, the zeolite mesh 33 is provided for filtering and absorbing volatile organic compound (VOC), and the high-efficiency particulate air filter 32 is provided for absorbing the chemical smog, bacteria, dusts, particles, and pollens contained in the polluted gas, thereby the polluted gas introduced into the filtering and cleaning assembly 3 is filtered and purified.

In some embodiments, the filtering and cleaning assembly 3 may be a combination of the activated carbon 31, the high-efficiency particulate air filter 32, the zeolite mesh 33, and a photocatalyst unit 34. In the present embodiment, the polluted gas is introduced into the filtering and cleaning assembly 3 so as to decompose and sterilize the hazardous matters in the polluted gas through the chemical energy converted from the light energy by the photocatalyst unit 34*a* and achieve the effect of filtration and purification by the filtering and cleaning assembly 3.

In some embodiments, the filtering and cleaning assembly 3 may be a combination of the activated carbon 31, the high-efficiency particulate air filter 32, the zeolite mesh 33, and a photo plasma unit 35. The photo plasma unit 35 includes a nanometer light tube. The polluted gas introduced by the filtering and cleaning assembly 3 is illuminated by the nanometer light tube, thereby the volatile organic gases contained in the polluted gas can be decomposed and purified. When the polluted gas is introduced into the filtering and cleaning assembly 3, the introduced polluted gas is illuminated by the nanometer light tube, making the oxygen molecules and water molecules in the polluted gas decompose into photo plasma with high oxidative power for generating a plasma flow which is capable of destroying the organic molecules. Accordingly, volatile organic compounds (VOC) such as formaldehyde and toluene in the polluted gas can be decomposed into water and carbon dioxide. Thus, the polluted gas can be filtered and purified by the filtering and cleaning assembly 3.

In another embodiment, the filtering and cleaning assembly 3 may be a combination of the activated carbon 31, the high-efficiency particulate air filter 32, the zeolite mesh 33, and a negative ion unit 36. The negative ion unit 36 includes a dust-collecting plate. Through applying high voltage discharging to the polluted gas introduced into the filtering and cleaning assembly 3, the particulates carry with positive charges in the polluted gas are adhered to the dust-collecting plate carry with negative charges. Accordingly, the polluted gas is filtered and purified by the filtering and cleaning assembly 3.

In some embodiments, the filtering and cleaning assembly 3 may be a combination of the activated carbon 31, the high-efficiency particulate air filter 32, the zeolite mesh 33, and a plasma ion unit 37. The plasma ion unit 37 generates a high-voltage plasma. Therefore, the viruses and the bacteria in the polluted gas introduced into the filtering and cleaning assembly 3 can be decomposed by the high-voltage plasma. Moreover, through the high-voltage plasma, when the polluted gas is introduced into the filtering and cleaning assembly 3, the oxygen molecules and the water molecules in the polluted gas are ionized to generate cations ($H^+$) and anions ($O_2^-$). After the substances attached with water molecules around the ions attach on the surfaces of viruses and bacteria and convert the water molecules into oxidative oxygen ions (hydroxyl ions, $OH^-$ ions) with high oxidative power under chemical reaction, and the oxidative oxygen ions take away the hydrogen ions of the proteins on the surfaces of the viruses and the bacteria so as to oxidize and decompose the microorganisms as mentioned above. Accordingly, the polluted gas is filtered and purified by the filtering and cleaning assembly 3.

In some embodiments, the filtering and cleaning assembly 3 may be the high-efficiency particulate air filter 32 only. Alternatively, in another embodiment, the filtering and cleaning assembly 3 may be any combination of the high-efficiency particulate air filter 32 and one of the photocatalyst unit 34, the photo plasma unit 35, the negative ion unit 36, and the plasma ion unit 37. In one embodiment, the filtering and cleaning assembly 3 may be a combination of the high-efficiency particulate air filter 32 and any two of the photocatalyst unit 34, the photo plasma unit 35, the negative ion unit 36, and the plasma ion unit 37. In one embodiment, the filtering and cleaning assembly 3 may be a combination of the high-efficiency particulate air filter 32 and any three of the photocatalyst unit 34, the photo plasma unit 35, the negative ion unit 36, and the plasma ion unit 37. In one embodiment, the filtering and cleaning assembly 3 may be a combination of the high-efficiency particulate air filter 32 and all of the photocatalyst unit 34, the photo plasma unit 35, the negative ion unit 36, and the plasma ion unit 37.

In brief, in some embodiments, the filtering and cleaning assembly 3 includes at least one selected from the group consisting of the activated carbon 31, the high-efficiency particulate air filter 32, the zeolite mesh 33, the photocatalyst unit 34, the photo plasma unit 35, the negative ion unit 36, the plasma ion unit 37, and any combination thereof.

The air pollution source (namely the polluted gas) may include at least one selected from the group consisting of particulate matters, carbon monoxide (CO), carbon dioxide ($CO_2$), ozone ($O_3$), sulfur dioxide ($SO_2$), nitrogen dioxide ($NO_2$), lead (Pb), total volatile organic compounds (TVOC), formaldehyde (HCHO), bacteria, fungi, viruses, and any combination thereof.

Please refer to FIG. 1A and FIG. 1B. The micro-controller 5 wirelessly receives the gas detection data of the at least one gas detection module 4 and performs an intelligent comparison under a surveillance condition. In one aspect of the present disclosure, the surveillance condition is defined as the gas detection data of the air pollution source detected by the at least one gas detection module 4 exceeding a safety detection value. In some embodiments, the safety detection value includes at least one selected from the group consisting of a concentration of PM2.5 which is less than 35 $\mu g/m^3$, a concentration of carbon dioxide which is less than 1000 ppm, a concentration of total volatile organic compounds which is less than 0.56 ppm, a concentration of formaldehyde which is less than 0.08 ppm, a colony-forming unit per cubic meter of bacteria which is less than 1500 $CFU/m^3$, a colony-forming unit per cubic meter of fungi which is less than 1000 $CFU/m^3$, a concentration of sulfur dioxide which is less than 0.075 ppm, a concentration of nitrogen dioxide which is less than 0.1 ppm, a concentration of carbon monoxide which is less than 9 ppm, a concentration of ozone which is less than 0.06 ppm, a concentration of lead which is less than 0.15 $\mu g/m^3$, and any combination thereof.

Please refer to FIG. 1 and FIG. 2. According to one or some embodiments of the present disclosure, a fresh air ventilation device for air pollution prevention is provided, so as to detect the air quality of the indoor space and verify the condition of the ambient air quality in real-time. At least one blower 2 is utilized to guide the air pollution source so as to filter the air pollution source through a filtering and cleaning assembly 3 in real-time. A micro-controller 5 is further provided to receive the data detected by the at least one gas detection module 4 to enable the at least one blower 2 and adjust the air volume of the at least one blower 2. Therefore, a fresh air ventilation device with an automatic-detection mode is provided so as to detect the ambient air quality and filter the air pollution source in real-time.

According to one or some embodiments, the present invention is further incorporated with cloud technology. Please refer to FIG. 1B, in some embodiments, the fresh air ventilation device may be connected to a cloud processing system 7. The micro-controller 5 is in data communication with the cloud processing system 7 wirelessly and bi-directionally, and the micro-controller 5 transmits the gas detection data detected by the gas detection module 4 of the fresh air ventilation device to the cloud processing system 7 and receives processing information transmitted from the cloud processing system 7, so that the micro-controller 5 transmits the driving command to enable the at least one blower 2 and adjust the air volume of the at least one blower 2.

It is noted that, for the embodiment shown in FIG. 1B and FIG. 2, the fresh air ventilation device can be in data communication with the cloud processing system 7 wirelessly and bi-directionally through the micro-controller 5 so as to transmit the gas detection data detected by the gas detection module 4 of the fresh air ventilation device to the cloud processing system 7 and receives the processed information transmitted from the cloud processing system 7, thereby transmitting the driving command to enable the at least one blower 2 and adjust the air volume of the at least one blower 2. Moreover, it is noted that, the enablement or the air volume of the at least one blower 2 can be manually controlled by the micro-controller 5 directly, or the air volume of the at least one blower 2 may be automatically and intelligently controlled by the cloud processing system 7 through the driving command. In other words, in some embodiments, when the gas detection data is much larger than the safety detection value, the adjustment amount for the air volume of the at least one blower 2 is much larger; while when gas detection data is much closer to the safety detection value, the adjustment amount for the air volume of the at least one blower 2 is much smaller. Moreover, in the embodiment that several fresh air ventilation devices of the present disclosure are installed in the same indoor space, the cloud processing system 7 also can transmit control signals to the respective fresh air ventilation devices according to different air quality conditions (i.e., based on the different gas detection data) detected by the gas detection modules 4 of the fresh air ventilation devices at different locations, so as to control the enablement of the at least one blower 2 and adjust the air volume of the at least one blower 2 of the fresh air ventilation device by the cloud processing system 7.

Please refer to FIG. 2, in some embodiments, the fresh air ventilation device may be connected to an air pollution processing system 6. The micro-controller 5 is in data communication with the air pollution processing system 6 wirelessly and bi-directionally, and the gas detection data detected by the gas detection module 4 of the fresh air ventilation device can be transmitted to the air pollution processing system 6 through the micro-controller 5. Alternatively, in some embodiments, the micro-controller 5 can receive the processed information transmitted from the air pollution processing system 6, so as to transmit the driving command to enable the at least one blower 2 and adjust the air volume of the at least one blower 2.

The air pollution processing system 6 comprises at least one outdoor gas detection module 6a, at least one indoor gas detection module 6b, the main body 1 of at least one fresh air ventilation device, at least one indoor cleaning and filtering device 6c, and an intelligent control-processing device 6d.

The at least one outdoor gas detection module 6a is disposed in an outdoor space B for detecting the air pollution source in the outdoor space B and transmitting an outdoor gas detection data. The at least one indoor gas detection module 6b is disposed in the indoor space A for detecting the air pollution source in the indoor space A and transmitting an indoor gas detection data. Moreover, it is noted that, the enablement or the air volume of the at least one blower 2 can be manually controlled through the micro-controller 5 directly, or the air volume of the at least one blower 2 may be automatically and intelligently controlled by the air pollution processing system 6 through the driving command. The outdoor gas detection module 6a detects an outdoor gas quality in the outdoor space B and transmits the outdoor gas detection data, also the indoor gas detection module 6b detects an indoor gas quality in the indoor space A and transmits the indoor gas detection data. The outdoor gas detection module 6a or the indoor gas detection module 6b may be equipped with the gas detection module 4 capable of detecting gas quality and outputting gas detection data.

The micro-controller 5 of the fresh air ventilation device for air pollution prevention controls whether an outdoor gas in the outdoor space B is introduced into the indoor space A or not, so as to perform the filtering and gas exchanging of the air pollution source in the indoor space A. The at least one indoor cleaning and filtering device 6c performs the filtering and gas exchanging of the air pollution source in the indoor space A. The intelligent control-processing device 6d includes a processor (not shown) and a communication transceiver (not shown) to receive the outdoor gas detection data and the indoor gas detection data and compare the outdoor gas detection data with the indoor gas detection data, and then intelligently and selectively control whether the fresh air ventilation device introduces the outdoor gas in the outdoor space B or not.

After the intelligent control-processing device 6d receives the outdoor gas detection data and the indoor gas detection data and compares the outdoor gas detection data with the indoor gas detection data, the intelligent control-processing device 6d intelligently and selectively controls whether the fresh air ventilation device introduces the outdoor gas in the outdoor space B or not. The intelligent control-processing device 6d controls the enablement of the at least one indoor cleaning and filtering device 6c in real-time to perform filtering and cleaning so as to allow the air pollution source in the indoor space A to be filtered and exchanged and become a clean air. It is noted that, the indoor cleaning and filtering device 6c may be a ventilator, a cooker hood, an electric fan, a cleaner, a vacuum cleaner, a blower fan, an air conditioner, or the like. Each of the indoor cleaning and filtering devices 6c is equipped with an indoor gas detection module 6b for detecting the air pollution source in the indoor space A and controlling the enablement and operation of the indoor cleaning and filtering device 6c.

Therefore, after the intelligent control-processing device 6d receives the outdoor gas detection data and the indoor gas detection data, compares the outdoor gas detection data with the indoor gas detection data, and determines that the indoor gas detection data is worse than the outdoor gas detection data, the intelligent control-processing device 6d transmits the control signal to the fresh air ventilation device to introduce the outdoor gas into the indoor space A and enable the at least one indoor cleaning and filtering device 6c to perform filtering and gas exchanging, but not limited thereto.

Moreover, it is noted that, after the intelligent control-processing device 6d receives the outdoor gas detection data and the indoor gas detection data and compares the outdoor gas detection data with the indoor gas detection data, the intelligent control-processing device 6d not only intelligently and selectively transmits a control command to the at least one indoor cleaning and filtering device 6c but also to the micro-controller 5 of the fresh air ventilation device to enable the at least one blower 2 and adjust the air volume of the at least one blower 2, so as to allow the air pollution source in the indoor space A to be filtered and exchanged and become a clean air.

In the embodiment shown in FIG. 2, at least three indoor gas detection modules 6b are provided. The intelligent control-processing device 6d receives and compares the indoor gas detection data detected by the at least three indoor gas detection modules 6b to perform intelligent computation and figure out a location containing the air pollution source in the indoor space A, accordingly, the intelligent control-processing device 6d intelligently and selectively enables the operation of a fresh air ventilation device or an indoor cleaning and filtering device 6c closest to the air pollution source so as to guide the air pollution source more quickly and prevent the air pollution source from spreading. Furthermore, in some other embodiments, the intelligent control-processing device 6d receives and compares the indoor gas detection data detected by the at least three indoor gas detection modules 6b to perform intelligent computation and figure out a location containing the air pollution source in the indoor space A, and the intelligent control-processing device 6d intelligently and selectively enables the operation of a fresh air ventilation device or an indoor cleaning and filtering device 6c closest to the air pollution source in a first priority, at the same time, the intelligent control-processing device 6d also performs intelligent computation to enable rest of the indoor cleaning and filtering devices 6c to generate a gas-flow for guiding the air pollution source in the indoor space A toward the indoor cleaning and filtering device 6c closest to the air pollution source for being filtered quickly.

According to one or some embodiments of the present disclosure, a fresh air ventilation device for air pollution prevention capable of detecting the air quality in the indoor space to verify the condition of the ambient air quality is provided. At least one blower is utilized to guide the air pollution source, so that the air pollution source can be filtered through a filtering and cleaning assembly in real-time. A micro-controller is further provided to receive the data detected by the at least one gas detection module to enable the at least one blower and adjust the air volume of the at least one blower, thereby the ambient air quality can be detected in real-time and the air pollution source can be filtered in real-time. Moreover, the fresh air ventilation device not only can detect the ambient air quality automatically but also can be connected to a cloud processing system or an indoor air pollution processing system to generate an integrated real-time air-processing system.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A fresh air ventilation device for air pollution prevention, wherein the fresh air ventilation device comprises:

a main body comprising an inlet channel and a gas-exchange channel;

a plurality of blowers, wherein one of the plurality of blowers is disposed in the main body to guide an air convection and to form a flow-guiding path in the inlet channel, and another of the plurality of blowers is disposed in the gas-exchange channel to perform a gas exchange through the gas-exchange channel;

a filtering and cleaning assembly disposed in the flow-guiding path to filter and clean an air pollution source in the air convection guided by the plurality of blowers; and at least one gas detection module disposed in the flow-guiding path of the main body to detect the air pollution source and transmit a gas detection data; and a micro-controller wirelessly connecting with the at least one gas detection module, wherein the micro-controller receives the gas detection data transmitted by the at least one gas detection module and performs a comparison to transmit a driving command to enable the plurality of blowers, and the micro-controller is in data communication with an air pollution processing system wirelessly and bi-directionally, wherein the air pollution processing system comprises:

a plurality of indoor gas detection modules disposed in an indoor space for detecting the air pollution source in the indoor space and transmitting a plurality of indoor gas detection data;

at least one indoor cleaning and filtering device for filtering and performing the gas exchange for the air pollution source in the indoor space;

the micro-controller of at least one fresh air ventilation device for air pollution prevention for controlling whether an outdoor gas in the outdoor space is introduced into the indoor space or not, so as to filter and perform the gas exchange for the air pollution source in the indoor space; and an intelligent control-processing device which receives and compares at least three of indoor gas detection data detected by at least three indoor gas detection modules to perform computation and figure out a location containing the air pollution source in the indoor space, and selectively enables at least one of the plurality of blowers or the at least one indoor cleaning and filtering device closest to the air pollution source, so as to guide the air pollution source more quickly and prevent the air pollution source from spreading.

2. The fresh air ventilation device for air pollution prevention according to claim 1, wherein the air pollution source comprises at least one selected from the group consisting of particulate matters, carbon monoxide, carbon dioxide, ozone, sulfur dioxide, nitrogen dioxide, lead, total volatile organic compounds, formaldehyde, bacteria, fungi, viruses, and any combination thereof.

3. The fresh air ventilation device for air pollution prevention according to claim 1, wherein the micro-controller performs the comparison under a surveillance condition to transmit the driving command to enable the plurality of blowers and adjust air volumes of the plurality of blowers.

4. The fresh air ventilation device for air pollution prevention according to claim 3, wherein the surveillance condition is defined as the gas detection data of the air pollution source detected by the at least one gas detection module exceeding a safety detection value.

5. The fresh air ventilation device for air pollution prevention according to claim 4, wherein the safety detection value includes at least one selected from the group consisting of a concentration of PM2.5 which is less than 35 $\mu g/m^3$, a concentration of carbon dioxide which is less than 1000 ppm, a concentration of total volatile organic compounds which is less than 0.56 ppm, a concentration of formaldehyde which is less than 0.08 ppm, a colony-forming unit per cubic meter of bacteria which is less than 1500 $CFU/m^3$, a colony-forming unit per cubic meter of fungi which is less than 1000 $CFU/m^3$, a concentration of sulfur dioxide which is less than 0.075 ppm, a concentration of nitrogen dioxide which is less than 0.1 ppm, a concentration of carbon monoxide which is less than 9 ppm, a concentration of ozone which is less than 0.06 ppm, a concentration of lead which is less than 0.15 $\mu g/m^3$, and any combination thereof.

6. The fresh air ventilation device for air pollution prevention according to claim 1, wherein the at least one gas detection module comprises a control circuit board, a gas detection main body, a microprocessor, and a communication device; the gas detection main body, the microprocessor, and the communication device are integrally packaged and electrically connected to the control circuit board; the microprocessor controls the operation of the gas detection main body, the gas detection main body detects the air pollution source and output a detection signal, and the microprocessor receives the detection signal to perform computation to generate and output the gas detection data to the communication device for transmitting outwardly.

7. The fresh air ventilation device for air pollution prevention according to claim 6, wherein the micro-controller wirelessly receives the gas detection data transmitted by the communication device.

8. The fresh air ventilation device for air pollution prevention according to claim 6, wherein the gas detection main body comprises:

a base, having:

a first surface;

a second surface opposite to the first surface;

a laser installation region hollowed out from the first surface to the second surface;

a gas inlet groove recessed from the second surface and located adjacent to the laser installation region, wherein the gas inlet groove has a gas inlet through hole and two lateral walls;

two light penetration windows penetrate on the two lateral walls of the gas inlet groove and are in communication with the laser installation region;

a gas-guiding component installation region recessed from the second surface and in communication with the gas inlet groove, wherein a ventilation hole penetrates a bottom surface of the gas-guiding component installation region; and a gas outlet groove including a first region and a second region, wherein the first region is corresponding to the gas-guiding component installation region and is recessed from a portion of the first surface corresponding to the bottom surface of the gas-guiding component installation region; the second region is hollowed out from the first surface to the second surface in a region that is not corresponding to the gas-guiding component installation region; the gas outlet groove is in communication with the ventilation hole and has a gas outlet through hole;

a piezoelectric actuator received in the gas-guiding component installation region;

a driving circuit board covering and attached to the second surface of the base;

a laser component disposed on and electrically connected to the driving circuit board, wherein the laser component is received in the laser installation region, and a light path of a light beam emitted by the laser component passes through the light penetration windows and is orthogonal to the gas inlet groove;

a particulate sensor disposed on and electrically connected to the driving circuit board, wherein the particulate sensor is received in a position of the gas inlet groove where the path of the light beam emitted by the laser component is orthogonal to the gas inlet groove, so that the particulates in the air pollution source passing through the gas inlet groove which is illuminated by the light beam of the laser component is detected by the particulate sensor;

a gas sensor disposed on and electrically connected to the driving circuit board, wherein the gas sensor is received in the gas outlet groove for detecting the air pollution source introduced into the gas outlet groove; and an outer cover covering the base and having a side plate, and the side plate has a gas inlet opening and a gas outlet opening, the gas inlet opening is corresponding to the gas inlet through hole of the base, and the gas outlet opening is corresponding to the gas outlet through hole of the base;

wherein when the outer cover is covered on the base and the driving circuit board is attached to the second surface of the base, a gas inlet path is defined by the gas inlet groove and a gas outlet path is defined by the gas outlet groove, thereby the piezoelectric actuator is driven to accelerate the introduction of the air pollution source outside the gas inlet through hole into the gas inlet path defined by the gas inlet groove from the gas inlet opening; the air pollution source passes through the particulate sensor to detect a particle concentration of the particulates contained in the air pollution source; and the air pollution source discharged into the gas outlet path defined by the gas outlet groove from the ventilation hole, detected by the gas sensor, and is discharged out of the gas detection main body from the gas outlet through hole and the gas outlet opening of the base.

9. The fresh air ventilation device for air pollution prevention according to claim 8, wherein the particulate sensor is capable of detecting particulate matters.

10. The fresh air ventilation device for air pollution prevention according to claim 8, wherein the gas sensor comprises at least one selected the group consisting of a volatile organic compound detector, a formaldehyde sensor, a bacterial sensor, a virus sensor, and any combination thereof; wherein the volatile organic compound detector is capable of detecting carbon dioxide or total volatile organic compounds; the formaldehyde sensor is capable of detecting formaldehyde (HCHO) gas; the bacterial sensor is capable of detecting bacteria or fungi; the virus sensor is capable of detecting viruses.

11. The fresh air ventilation device for air pollution prevention according to claim 8, wherein the gas sensor comprises a temperature and humidity sensor, and the temperature and humidity sensor is capable of detecting the temperature and humidity of the air pollution source.

12. The fresh air ventilation device for air pollution prevention according to claim 3, wherein the micro-controller is in data communication with a cloud processing system wirelessly and bi-directionally, and the micro-controller transmits the gas detection data detected by the at least one gas detection module of the fresh air ventilation device to the cloud processing system and receives processed information transmitted from the cloud processing system, so that the micro-controller transmits the driving command to enable the plurality of blowers and adjust the air volumes of the plurality of blowers.

13. The fresh air ventilation device for air pollution prevention according to claim 3, wherein the micro-controller transmits the gas detection data detected by the at least one gas detection module of the fresh air ventilation device to the air pollution processing system and receives processed information transmitted by the air pollution processing system, so that the micro-controller transmits the driving command to enable the plurality of blowers and adjust the air volumes of the plurality of blowers.

14. The fresh air ventilation device for air pollution prevention according to claim 13, wherein the air pollution processing system comprises:

at least one outdoor gas detection module, wherein the at least one outdoor gas detection module is disposed in an outdoor space for detecting the air pollution source in the outdoor space and transmitting an outdoor gas detection data, wherein after the intelligent control-processing device receives the outdoor gas detection data and the plurality of indoor gas detection data and compares the outdoor gas detection data with the plurality of indoor gas detection data, the intelligent control-processing device selectively controls whether the outdoor gas in the outdoor space is introduced by the at least one fresh air ventilation device or not, and the intelligent control-processing device controls whether the at least one indoor cleaning and filtering device is enabled in real-time for filtering and cleaning so as to allow the air pollution source in the indoor space to be filtered and gas exchanged into clean air.

15. The fresh air ventilation device for air pollution prevention according to claim 14, wherein after the intelligent control-processing device receives the outdoor gas detection data and the plurality of indoor gas detection data and compares the outdoor gas detection data with the plurality of indoor gas detection data, the intelligent control-processing device selectively transmits a control command to the micro-controller of the at least one fresh air ventilation device, therefore the micro-controller transmits the driving command to enable the plurality of blowers and adjust the air volumes of the plurality of blowers, so as to allow the air pollution source in the indoor space to be filtered and gas exchanged into clean air.

16. The fresh air ventilation device for air pollution prevention according to claim 14, wherein the rest of the fresh air ventilation device or the indoor cleaning and filtering device other than the one closest to the air pollution source is selectively enabled by the intelligent control-processing device, so as to generate a gas-flow for guiding the air pollution source in the indoor space toward the fresh air ventilation device or the indoor cleaning and filtering device closest to the air pollution source for being filtered quickly.

17. The fresh air ventilation device for air pollution prevention according to claim 1, wherein the filtering and cleaning assembly comprises at least one selected from the group consisting of an activated carbon, a high-efficiency particulate air filter, a zeolite mesh, and any combination thereof.

18. The fresh air ventilation device for air pollution prevention according to according to claim 1, wherein the filtering and cleaning assembly is coated with at least one selected from the group consisting of a cleansing factor layer having chlorine dioxide, a herbal protection coating layer including the extracts of *Rhus chinensis* Mill and the extracts of *Ginkgo biloba*, a layer of silver ions, and any combination thereof wherein the cleaning factor layer suppresses viruses and bacteria in the air pollution source; the herbal protection coating layer forms a herbal protection anti-allergy filter which can efficiently perform an anti-allergy function and destroy cell surface proteins of influenza viruses passing through the herbal protection anti-allergy filter; the layer of silver ions suppresses viruses and bacteria in the air pollution source.

19. The fresh air ventilation device for air pollution prevention according to claim 17, wherein the filtering and cleaning assembly comprises at least one selected from the group consisting of the activated carbon, the high-efficiency particulate air filter, the zeolite mesh, a photocatalyst unit, a photo plasma unit, a negative ion unit, a plasma ion unit, and any combination thereof.

\* \* \* \* \*